(12) United States Patent
Malevich et al.

(10) Patent No.: US 9,611,554 B2
(45) Date of Patent: Apr. 4, 2017

(54) PRODUCTION OF HYDROCARBONS FROM PLANT OIL AND ANIMAL FAT

(71) Applicant: ALTRANEX CORPORATION, Kingston (CA)

(72) Inventors: Dzmitry Malevich, Kingston (CA); Graham Thomas Thornton Gibson, Kingston (CA)

(73) Assignee: ADVONEX INTERNATIONAL CORP., Ontario (CA)

(*) Notice: Subject to any disclaimer, the term of this patent is extended or adjusted under 35 U.S.C. 154(b) by 8 days.

(21) Appl. No.: 14/854,782

(22) Filed: Sep. 15, 2015

(65) Prior Publication Data
US 2016/0076157 A1 Mar. 17, 2016

Related U.S. Application Data

(60) Provisional application No. 62/050,198, filed on Sep. 15, 2014.

(51) Int. Cl.
| | |
|---|---|
| *C10G 1/00* | (2006.01) |
| *C07C 6/04* | (2006.01) |
| *C07C 5/23* | (2006.01) |
| *C25B 3/10* | (2006.01) |
| *C10L 1/04* | (2006.01) |
| *C10M 105/04* | (2006.01) |

(52) U.S. Cl.
CPC .............. *C25B 3/10* (2013.01); *C07C 6/04* (2013.01); *C10L 1/04* (2013.01); *C10M 105/04* (2013.01); *C10L 2200/0469* (2013.01); *C10L 2270/023* (2013.01); *C10L 2270/026* (2013.01); *C10L 2270/04* (2013.01); *C10L 2290/38* (2013.01)

(58) Field of Classification Search
CPC ................ C10G 1/00; C07C 6/04; C07C 5/23
USPC .......................... 585/240, 242, 643, 664, 324
See application file for complete search history.

(56) References Cited

U.S. PATENT DOCUMENTS

2012/0197050 A1 8/2012 Joshi et al.

FOREIGN PATENT DOCUMENTS

WO   WO 2011/133906   10/2011

OTHER PUBLICATIONS

International Search Report and Written Opinion for International (PCT) Patent Application No. PCT/CA2015/050888, mailed Dec. 2, 2015, 8 pages.

*Primary Examiner* — Thuan D Dang
(74) *Attorney, Agent, or Firm* — Sheridan Ross P.C.

(57) ABSTRACT

Oils from plants and animal fats are hydrolyzed to fatty acids for a Kolbe reaction. The invention relates to a high productivity Kolbe reaction process for electrochemically decarboxylating C4-C28 fatty acids derived from sources selected based on their saturated and unsaturated fatty acid content in order to lower anodic passivation voltage during synthesis of C6-C54 hydrocarbons. The C6-C54 hydrocarbons may undergo olefin metathesis and/or hydroisomerization reaction processes to synthesize heavy fuel oil, diesel fuel, kerosene fuel, lubricant base oil, and linear alpha olefin products useful as precursors for polymers, detergents, and other fine chemicals.

20 Claims, 11 Drawing Sheets

PRODUCTION OF HYDROCARBONS FROM PLANT OIL AND ANIMAL FAT

CROSS REFERENCE TO RELATED APPLICATION

This application claims the benefit of priority under 35 U.S.C. §119(e) to U.S. Provisional Patent Application Ser. No. 62/050,198 filed Sep. 15, 2014, which is incorporated herein by reference.

FIELD OF THE INVENTION

Oils from plants and animal fats are hydrolyzed to fatty acids for a Kolbe reaction. The invention relates to a Kolbe reaction process for electrochemically decarboxylating C4-C28 fatty acids with high productivity by carefully selecting feedstock oils from plants and animal fats based on their fatty acid composition to lower anodic passivation voltage and synthesizing C6-C54 hydrocarbons. The C6-C54 undergo olefin metathesis and/or hydroisomerization reaction processes to synthesize heavy fuel oil, diesel fuel, kerosene fuel, lubricant base oil, and linear alpha olefin products useful as precursors for polymers, detergents, and other fine chemicals.

BACKGROUND OF THE INVENTION

The statements in this background section may be useful to an understanding of the invention, but may not constitute prior art.

World-wide production of petroleum is expected to peak around year 2020 and decline thereafter which could cause a global economic decline after 2020. Needed are substitute hydrocarbon sources to petroleum. Inventing alternative, large-scale processes for production of hydrocarbons is needed. These processes need to be economical to be incorporated successfully in free market economies. Research is underway to identify substitute processes and feedstocks for these processes that can be used in large-scale production of needed hydrocarbons. Alternative and renewable feedstocks are being explored for use in economical chemical processes to make hydrocarbons such as fuel oil, diesel fuel, kerosene fuel, lubricant base oil and linear alpha olefins. These particular hydrocarbons are currently obtained from processing petroleum.

Some alternative and renewable feedstocks are plant oils, microbial-produced oils and fatty acids, and animal fats. Feedstocks such as plant oils and animal fats are triglycerides that can be processed using ester hydrolysis, Kolbe electrolysis, olefin metathesis and hydroisomerization to produce fuel oil, diesel fuel, kerosene fuel, lubricant base oil and linear alpha olefins. Ester hydrolysis may be used to convert oils and fats which contain triglycerides to free fatty acids (FFAs). The fatty acids may be decarboxylated and converted into larger hydrocarbons by Kolbe electrolysis. The alkene hydrocarbons produced from Kolbe electrolysis may be reacted by olefin metathesis using catalysts to redistribute the alkenes by a scission and a regeneration of carbon-carbon double bonds. The linear alkene hydrocarbons formed from olefin metathesis using catalysts may be hydroisomerized to add hydrocarbon branches.

There are many plant oils which can be obtained in large amounts from crop plants. Table 1 below indicates the volumetric (liters and gallons) amounts which can be obtained from crops per hectare or acre. Recycled food oils are also being used as a feedstock to produce the aforementioned hydrocarbons.

TABLE 1

Amounts of Plant Oils That Have Been Obtained From Various Crop Plants

| Crop | liters oil/hectare | US gal/acre |
|---|---|---|
| corn (maize) | 172 | 18 |
| cashew nut | 176 | 19 |
| oats | 217 | 23 |
| lupine | 232 | 25 |
| kenaf | 273 | 29 |
| *calendula* | 305 | 33 |
| cotton | 325 | 35 |
| hemp | 363 | 39 |
| soybean | 446 | 48 |
| coffee | 459 | 49 |
| linseed (flax) | 478 | 51 |
| hazelnut | 482 | 51 |
| *euphorbia* | 524 | 56 |
| pumpkin seed | 534 | 57 |
| coriander | 536 | 57 |
| mustard seed | 572 | 61 |
| *camelina* | 583 | 62 |
| sesame | 696 | 74 |
| safflower | 779 | 83 |
| rice | 828 | 88 |
| tung oil | 940 | 100 |
| sunflower | 952 | 102 |
| cocoa (cacao) | 1026 | 110 |
| peanut | 1059 | 113 |
| opium poppy | 1163 | 124 |
| rapeseed | 1190 | 127 |
| olive | 1212 | 129 |
| castor bean | 1413 | 151 |
| pecan nut | 1791 | 191 |
| jojoba | 1818 | 194 |
| *jatropha* | 1892 | 202 |
| macadamia nut | 2246 | 240 |
| brazil nut | 2392 | 255 |
| avocado | 2638 | 282 |
| coconut | 2689 | 287 |
| oil palm | 5950 | 635 |

Plant oils and animal fat (such as beef tallow or lard) contain a mixture of triglycerides which can be hydrolyzed to obtain various fatty acids. Most plant oil-derived and animal fat-derived FFAs typically have 10-20 carbon atoms with zero, one, two or three carbon-carbon double bonds.

The Kolbe electrolysis reaction is a chemical reaction process for the decarboxylation of fatty acids in processes making hydrocarbons. The Kolbe electrolysis reaction process may use a single fatty acid or fatty acid mixtures. A significant renewable source of the fatty acids comes from the hydrolysis of triglycerides of plant oils and animal fats.

There are problems in using the Kolbe electrolysis reaction to produce hydrocarbons from fatty acids. The problems include a development of a passivation voltage (a voltage drop at the Kolbe cell electrodes during the Kolbe electrolysis reaction) which requires higher cell voltage which results in consumption of large quantities of electricity. If plant oils and animal fats are to be an economically viable source from which hydrocarbons may be produced, then the Kolbe electrolysis reaction needs to be improved in terms of its electrical usage efficiency.

It is against this background that the various embodiments of the present invention were developed.

SUMMARY OF THE INVENTION

It has been observed that the development of the passivation voltage during a Kolbe electrolysis reaction is dependent on the type of carboxylic acid substrate. As noted above, there is an important need to lower wasteful electrical usage by the Kolbe reaction process, which the present inventors have accomplished by exploiting the correlation between the fatty acid composition of the feedstock and the reduction of passivation voltage, as described in detail herein.

In preferred embodiments, the present invention involves a method of increasing productivity of a Kolbe electrolysis reaction forming one or more C6 to C54 hydrocarbons, the method comprising: combining one or more C4-C28 fatty acids with a solvent to create a reaction mixture and performing a high productivity Kolbe electrolysis reaction on the reaction mixture to produce the C6 to C54 hydrocarbon or the C6 to C54 hydrocarbons, wherein the source or sources of the fatty acids in the reaction mixture are carefully selected based on their fatty acid composition to reduce passivation of an electrode used in the Kolbe electrolysis reaction. The source of the C4-C28 fatty acid or a mixture of C4-C28 fatty acids may be a plant oil, an animal fat, or a microbial oil.

In other preferred embodiments, the present invention provides a method of producing C6-C54 hydrocarbons comprising: (a) combining one or more C4-C28 unsaturated fatty acids and one or more C4-C28 saturated fatty acids with a solvent; and (b) performing a Kolbe electrolysis reaction on the combined reaction mixture prepared in (a) to produce one or more C6 to C54 hydrocarbons, wherein the combined reaction mixture of the unsaturated and saturated fatty acids has a combined saturation score (S) of greater than 1.0, where:

$$S=(2w_s+w_{mu})/(w_{mu}+2w_{du}+3w_{tu})$$

and $w_s$, $w_{mu}$, $w_{du}$ and $w_{tu}$ are weight percent of fatty acids that are saturated ($w_s$), and having one ($w_{mu}$), two ($w_{du}$) or three ($w_{tu}$) double bonds, respectively.

In other preferred embodiments, the present invention provides a method of increasing productivity of a Kolbe electrolysis reaction forming one or more C6 to C54 hydrocarbons, the method comprising: (i) combining one or more C4-C28 unsaturated fatty acids with a solvent to create a reaction mixture; (ii) adding one or more C4-C28 saturated fatty acids to the reaction mixture; and (iii) performing a Kolbe electrolysis reaction on the combined reaction mixture to produce one or more C6 to C54 hydrocarbons, wherein the saturated fatty acids are added to lower a passivation voltage of an electrode used in the Kolbe electrolysis reaction, and wherein the combined reaction mixture has a combined saturation score (S) of greater than 1.0, where:

$$S=(2w_s+w_{mu})/(w_{mu}+2w_{du}+3w_{tu})$$

and $w_s$, $w_{mu}$, $w_{du}$ and $w_{tu}$ are weight percent of fatty acids that are saturated ($w_s$), and having one ($w_{mu}$), two ($w_{du}$) or three ($w_{tu}$) double bonds, respectively.

In other embodiments of the present invention the solvent is a C1 to C4 alcohol, methanol, ethanol, propanol, isopropanol, butanol, water, or a mixture thereof In certain embodiments the solvent is a mixture that contains between about 0.5 percent to about 50 percent water by volume. In instances where the initial solvent is a pure alcohol, it becomes a mixture with water as water is produced when the fatty acids are partially neutralized with base.

In other embodiments of the present invention the reaction mixture for the Kolbe electrolysis reaction may not be a solution at room temperature. During the Kolbe electrolysis reaction, the neutralized (i.e., salt) form of the fatty acid must be in solution. The free fatty acid can exist as a separate phase. As the carboxylate ion form of the fatty acid is converted to hydrocarbon during electrolysis, the base, which is formed in this reaction, reacts with the free fatty acid to form a salt, thereby drawing more fatty acid (in its salt form) into solution. This continues until all the fatty acid is consumed.

In other embodiments of the present invention the C4-C28 fatty acid in the solvent or the mixture of C4-C28 fatty acids in the solvent are reacted with a base to form an amount of a salt of the C4-C28 fatty acid in the solvent or the mixture of C4-C28 fatty acids.

In other embodiments of the present invention an electrolyte is added to the reaction mixture to improve electrical conductivity of the Kolbe electrolysis reaction. The electrolyte is selected from the group consisting of a perchlorate salt, a p-toluenesulfonate salt, a tetrafluoroborate salt, and a mixture thereof.

In other embodiments of the present invention the Kolbe electrolysis reaction is conducted at a temperature in the range of about 15° C. to about 100° C.

In other embodiments of the present invention a pressure other than atmospheric pressure may be imposed on the reaction mixture during the Kolbe electrolysis reaction to change a rate of loss of the solvent or a volatile fatty acid.

In other embodiments of the present invention current supplied to electrodes is 0.05-1.0 amperes/cm$^2$ area of the electrodes.

In other embodiments of the present invention the reacting surface of the anode electrode is a platinum group metal such as platinum, iridium, palladium, ruthenium, rhodium, or osmium or is a carbon material such as graphite, glassy carbon, baked carbon; or is a mixture of a platinum group metal and a carbon material.

In other embodiments the present invention also involves following the Kolbe electrolysis reaction with an olefin metathesis reaction using a C2-C5 aliphatic alkene or mixtures thereof. The olefin metathesis reaction modifies a chain length of a hydrocarbon and produces a linear alpha olefin or branched hydrocarbons.

In other embodiments the present invention also involves following the Kolbe electrolysis reaction with an ethenolysis reaction using ethene to obtain 1-decene, 1-heptene, 1-butene, 1-octene, 1-hexene and/or 1,4-pentadiene.

In other embodiments the present invention also involves separating the products of the ethenolysis reaction to obtain 1-decene, 1-heptene, 1-butene, 1,4-pentadiene, a diesel fuel, and a heavy fuel oil.

In other embodiments of the present invention, the method comprises the step of separating the products from the Kolbe electrolysis reaction, which are an amount of diesel fuel and a heavy fuel oil. Following separation from Kolbe electrolysis reaction mixture, the diesel fuel and heavy fuel components will separate, or will be separated, from one another.

In other embodiments the present invention also involves hydroisomerizing the heavy fuel oil to produce a lubricant base oil.

In other embodiments of the present invention, the hydroisomerization reaction uses a catalyst which is a silica/alumina-based zeolite containing impregnated platinum, a reaction temperature between about 250° C. to about 400° C., a reaction pressure between about 10 bar to about 400 bar, and a hydrogen gas to a hydrocarbon ratio of about 2 to about 50.

In other embodiments of the present invention the reaction mixture uses a solvent and a base from a preceding hydrolysis reaction of a triglyceride.

In other embodiments of the present invention the concentration of the C4-C28 fatty acid in the Kolbe electrolysis reaction is between about a 0.01 mole/litre to about a 1 mole/litre.

In preferred embodiments of the present invention the solvent is methanol, ethanol, or isopropanol.

Other embodiments of the present invention will become apparent from the detailed description of the invention when read in conjunction with the drawings.

BRIEF DESCRIPTION OF THE DRAWINGS

The invention can be further understood by referring to the drawings which represent certain embodiments of the invention.

In FIG. 1a named are sequential hydrolysis and Kolbe electrolysis processes to make hydrocarbons that can be used as a heavy fuel oil. In FIG. 1b named are sequential hydrolysis, Kolbe electrolysis, olefin metathesis, and separation processes to make hydrocarbons suitable for diesel fuel, heavy fuel oil, and shorter linear alpha olefins that can be used as a kerosene fuel or can be used as precursors for advanced polymers, detergents and other fine chemicals. In FIG. 1c named are sequential hydrolysis, Kolbe electrolysis, a separation, and hydroisomerization processes to make hydrocarbons useful as lubricant base oil.

DETAILED DESCRIPTION OF THE INVENTION

The present invention relates to methods and processes for the production of hydrocarbon compositions at least substantially oxygen-free and made from sustainable plant oils, microbial oils, animal fats and combinations thereof. These hydrocarbon compositions can be used in a wide variety of applications. In particular, the hydrocarbon compositions can be employed as fuel for use in passenger and heavy-duty ground transportation vehicles, such as industrial trucks, railroads and the like, cargo and cruise ships and the like, and in aircraft, such as airplanes, helicopters, and the like. Further, the hydrocarbon compositions can be used as a replacement for heating oil to heat houses and the like.

Figure 1A:
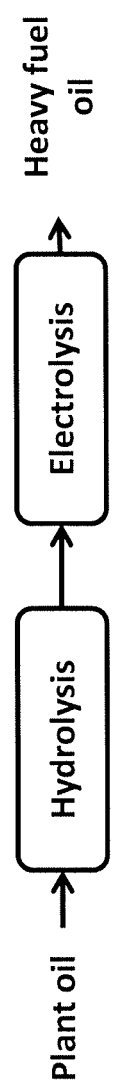
FIGS. 1a, 1b, and 1c depict sequential process steps of the invention for making various hydrocarbons.
Figure 1B:
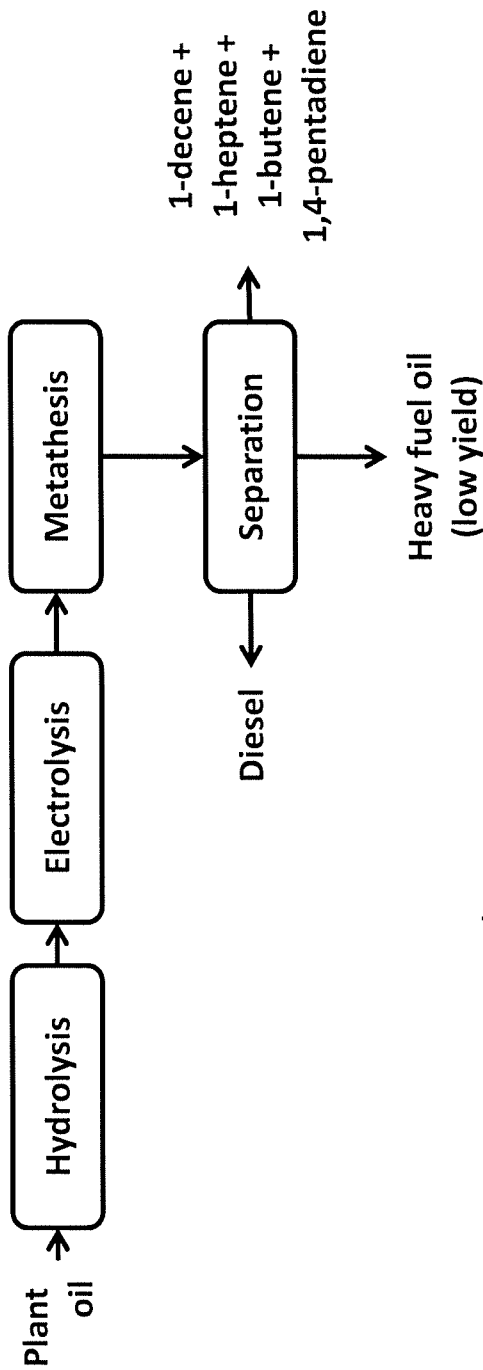
Figure 1C:
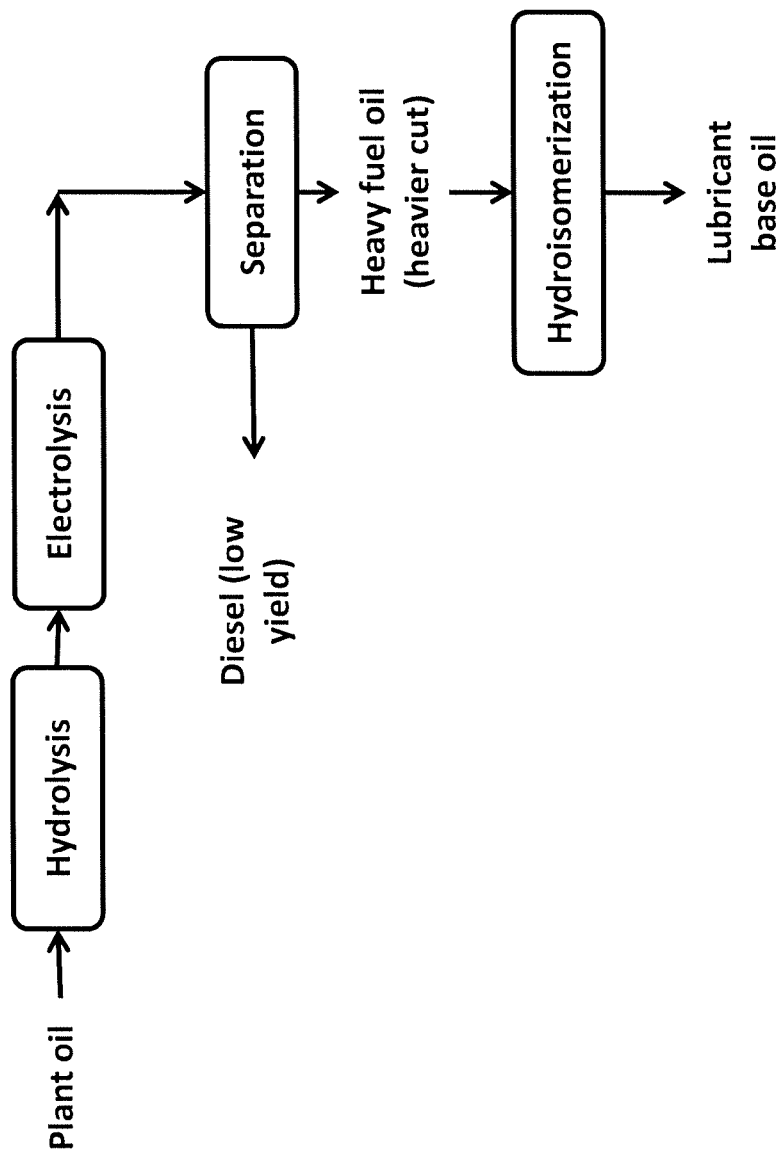

In one aspect, the present invention provides a specialized use of several chemical processes for making heavy fuel oil, diesel fuel, kerosene fuel, lubricant base oil, and linear alpha olefins useful as precursors, from plant oils, microbial oils, animal fats, or combinations thereof. These chemical processes include hydrolysis and Kolbe electrolysis, and, optionally, olefin metathesis and/or hydroisomerization. FIG. 1a, FIG. 1b, and FIG. 1c depict sequential process steps of the invention for making various hydrocarbons. In FIG. 1a named are sequential hydrolysis and Kolbe electrolysis processes to make hydrocarbons that can be used as a heavy fuel oil. In FIG. 1b named are sequential hydrolysis, Kolbe electrolysis, olefin metathesis, and separation processes to make hydrocarbons suitable for diesel fuel, heavy fuel oil, and shorter linear alpha olefins that can be used as a kerosene fuel or used as precursors for advanced polymers, detergents and other fine chemicals. In FIG. 1c named are sequential hydrolysis, Kolbe electrolysis, separation, and hydroisomerization processes to make hydrocarbons useful as a lubricant base oil.

As described herein, hydrolysis and Kolbe electrolysis, alone or in together with olefin metathesis and/or hydroisomerization can be combined in an overall process to make hydrocarbons useful for different applications, including renewable replacements for middle-distillate fuels, heavy fuels, lubricant base oil and linear alpha olefins. Olefin metathesis may be performed prior to hydrolysis or after electrolysis and lead to the same end products. The hydrocarbons produced from these chemical processes are derived from a biological source selected from the group consisting of plant oil, microbial oils, animal fats and combinations thereof and wherein each hydrocarbon composition is at least substantially free of oxygen.

Hydrolysis

The hydrolysis step can comprise acid-catalyzed hydrolysis, base-catalyzed hydrolysis or steam hydrolysis or other methods that efficiently convert the plant oil, microbial oil and animal fat into free fatty acids and glycerol. Optionally, the overall process comprises more than one type of hydrolysis.

The catalyst used in the hydrolysis reaction can be selected from a wide variety, including acids and bases or, as in the case for steam hydrolysis, the hydrolysis reaction can be conducted without a catalyst. Further, the reaction can include the application of heat to improve solubility and accelerate the reaction. The preferred embodiment for large-scale hydrolysis of thermally stable fats and oils is counter-current steam hydrolysis, e.g., the Colgate-Emery process, which efficiently leads to high yields of free fatty acids.

Figure 2:
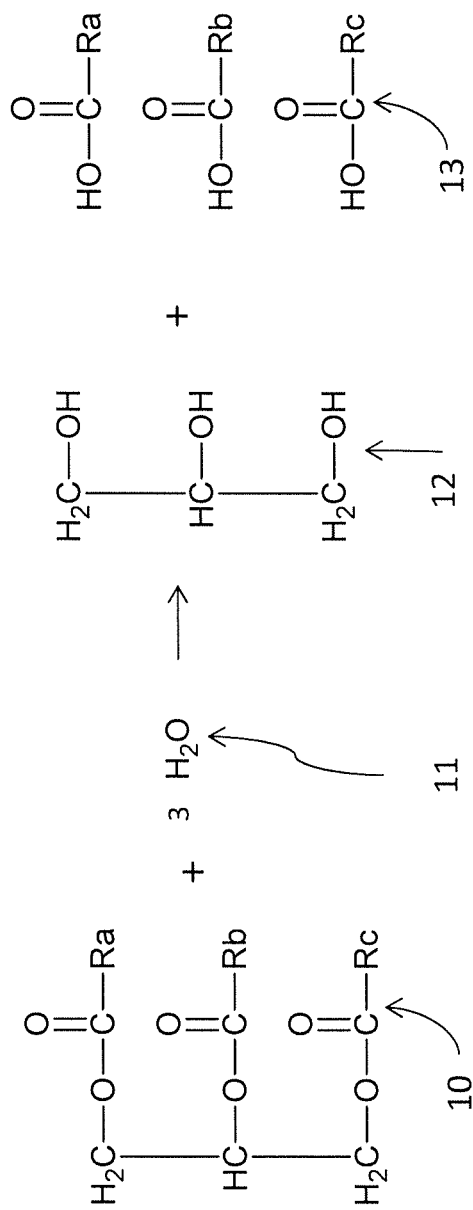
FIG. 2 depicts a hydrolysis reaction of a triglyceride and water to produce free fatty acids and glycerol which is a process step which may be practiced in accordance with certain embodiments of the invention.

FIG. 2 depicts a chemical structure diagram to show a hydrolysis reaction of a triglyceride and water to produce free fatty acids and glycerol which is a process step which may be practiced in accordance with certain embodiments of the invention. As shown in FIG. 2, a triglyceride 10 is reacted with water 11 to produce glycerol 12 and fatty acids 13. In the reaction example in FIG. 2, the triglyceride 10 includes substituents $R_a$, $R_b$, and $R_c$, where $R_a$, $R_b$, and $R_c$ are each, independently, H, an aliphatic substituent or a substituted aliphatic substituent. The term "aliphatic," as used herein, refers to a non-aromatic substituent composed of hydrogen and carbon. The aliphatic substituent can be saturated, in which the carbons are joined by single bonds only (alkyl), or unsaturated, in which at least one pair of carbons is joined by a double (alkenyl) or triple bond (alkenyl). Short chain fatty acids are fatty acids with aliphatic tails of fewer than six carbons. Medium chain fatty acids are fatty acids with aliphatic tails of 6-12 carbons. Long chain fatty acids have aliphatic tails for 13 to 21 carbon atoms. Very long chain fatty acids have aliphatic tails of 22 or more carbons."

A triglyceride is the prevalent component of plant or animal fats. Typical plant oils are a mixture of triglycerides which have commonly three linear hydrocarbon chains as depicted in FIG. 2 by substituents $R_a$, $R_b$, and $R_c$. The free fatty acids following hydrolysis of typical plant triglycerides have 10, 12, 14, 16, 18, 20, 22, or 24 carbons or a mixture of these carbon numbers. The present invention may also use a monoglyceride or a diglyceride. The substituents $R_a$, $R_b$, and $R_c$ of the glyceride do not need to have all three substituents be fatty acid esters, e.g., one glyceryl substituent may be a substituted aliphatic group that contains one or more alternative functional groups that include the elements phosphorus, oxygen, or nitrogen.

For some embodiments of the present invention the free fatty acids produced from the hydrolysis reaction contain an even number of carbon atoms, from 4 to 28 bonded in an unbranched chain. Most of the bonds between the carbon atoms in the single fatty acid chain will be single carbon-carbon bonds. When the bonds in the fatty acid chain are all single bonds, then the free fatty acid is called a saturated fatty acid. In unsaturated fatty acids at least one bond between adjacent carbon atoms is a double bond. In poly-unsaturated fatty acids, the fatty acid chain has multiple carbon-carbon double bonds.

Listed in the leftmost column of Table 2 are examples of sources of oils and fats (triglycerides). Free fatty acids (FFAs) are obtained from these triglycerides by hydrolysis as used in some embodiments of the present invention, and the natural composition of FFAs in the oil or fat from a given source is included in Table 2. In Table 2, the designation of the fatty acid is Cx:y where x is the number of carbon atoms and y is the number of carbon-carbon double bonds (unsaturation) in the fatty acid molecule.

TABLE 2

Plant oils and animal fats and their FFA percent composition
(from http://www.chempro.in/fattyacid.htm)

| Source | ≤C12:0 | C14:0 | C16:0 | C18:0 | C18:1 | C18:2 | C18:3 | ≥C20:0 |
|---|---|---|---|---|---|---|---|---|
| Canola | | | 4.0 | 2.0 | 62.0 | 22.0 | 10.0 | |
| Coconut | 58.3 | 20.6 | 9.2 | 3.0 | 7.2 | 1.7 | | |
| Corn | | | 11.0 | 2.0 | 28.0 | 58.0 | 1.0 | |
| Cottonseed | | 1.0 | 22.0 | 3.0 | 19.0 | 54.0 | 1.0 | |
| Flaxseed | 2.7 | 1.0 | 5.1 | 4.6 | 24.3 | 16.3 | 45.1 | 0.9 |
| Jatropha | | 0.1 | 14.2 | 7.0 | 44.7 | 32.8 | 0.3 | 0.2 |
| Lard | | 2.0 | 26.0 | 14.0 | 44.0 | 10.0 | | |
| Mustard seed | | | 1.5 | 0.4 | 22.0 | 14.2 | 6.8 | 47.0 |
| Olive Oil | | | 13.0 | 3.0 | 71.0 | 10.0 | 1.0 | |
| Palm | | 1.0 | 45.0 | 4.0 | 40.0 | 10.0 | | |
| Palm Kernel | 52.0 | 16.0 | 8.0 | 3.0 | 15.0 | 2.0 | | |
| Peanut | | | 11.0 | 2.0 | 48.0 | 32.0 | | |
| Sesame | | | 9.0 | 4.0 | 41.0 | 45.0 | | |
| Soybean | | | 11.0 | 4.0 | 24.0 | 54.0 | 7.0 | |
| Sunflower | | | 6.2 | 3.7 | 25.2 | 63.1 | 0.2 | 1.5 |
| Tallow | | 3.0 | 24.0 | 19.0 | 43.0 | 3.0 | 1.0 | |

Kolbe Electrolyis

The Kolbe electrolysis reaction is a known useful process for the decarboxylation of fatty acids derived from the hydrolysis of triglycerides of plant oils and animal fats. However, there are problems in using the Kolbe electrolysis reaction to produce hydrocarbons from fatty acids. A particular drawback associated with the Kolbe electrolysis reaction, which hinders its adoption in commercial processes, is the development of a passivation voltage in the Kolbe electrolysis reaction cell, which results in a waste of electricity in the Kolbe process.

Figure 3:
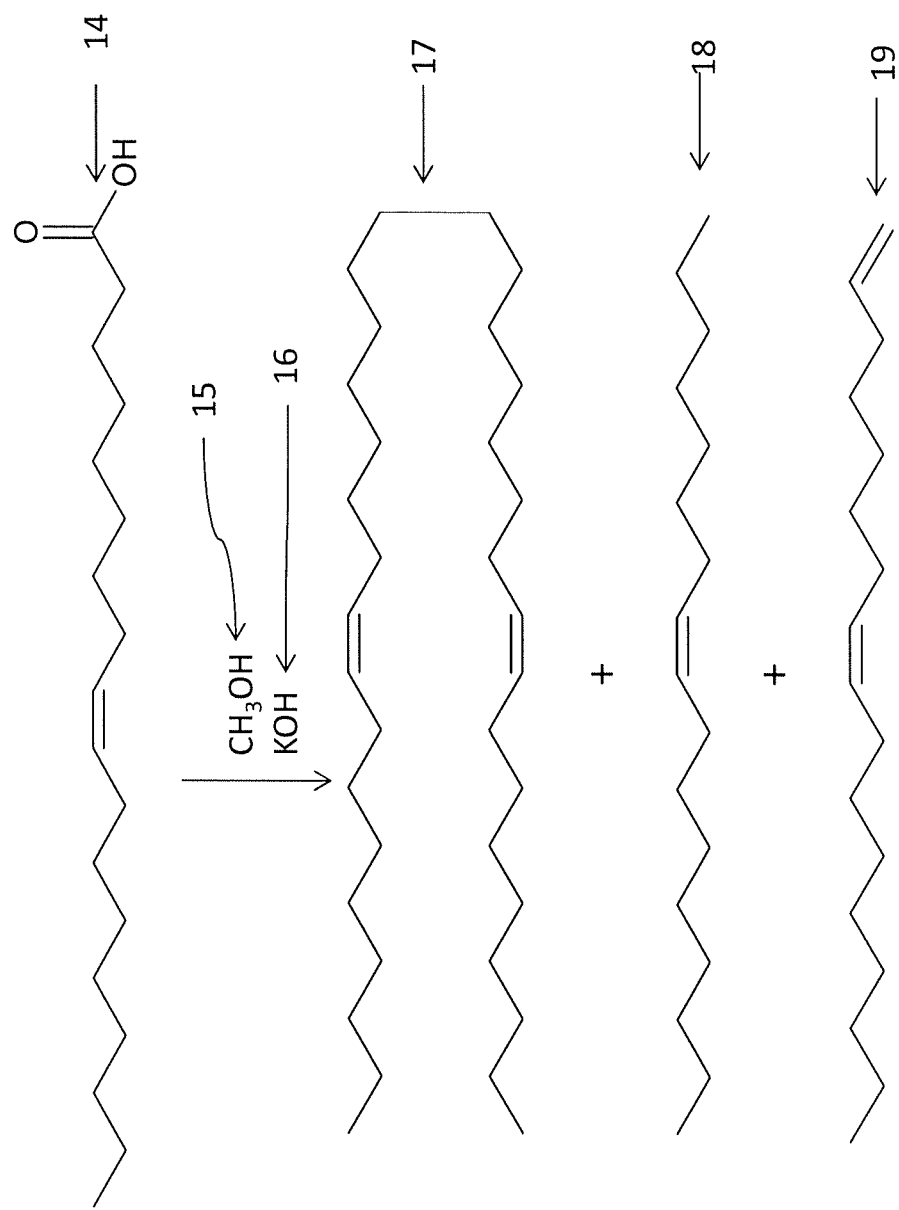
FIG. 3 depicts a Kolbe electrolysis reaction of oleic acid, a free fatty acid, with methanol and potassium hydroxide into three different linear hydrocarbons which is a process step which may be practiced in accordance with certain embodiments of the invention.

Kolbe electrolysis is a reaction to electrochemically oxidize carboxylic acids to produce alkanes, alkenes, alkane-containing products, alkene-containing products (i.e., compounds that comprise alkanes and alkene, respectively, such as substituted alkanes and substitute alkenes, generated from the Kolbe electrolysis reaction) and mixtures thereof. The reaction proceeds through radical intermediates to yield products based on dimerization of these radicals, such that an n-carbon acid will combine with an m-carbon acid to form an alkane and/or alkene of length (m+n−2) carbons along with two carbon dioxide molecules and one hydrogen molecule. The radical intermediates also lead to shorter alkane and/or alkene products by disproportionation. In the Kolbe electrolysis, only the carboxyl groups participate in the reaction and any unsaturation that may be present in the fatty acid chain is preserved in the final product. FIG. 3 shows a Kolbe electrolysis reaction in accordance with certain embodiments of the invention. As shown in FIG. 3, oleic acid 14 is reacted in Kolbe electrolysis in solvent methanol 15 in the presence of base potassium hydroxide 16 to produce cis,cis-9,25-tetratriacontadiene 17, in addition to small amounts of disproportionation products 18 and 19.

In Kolbe electrolysis, homocoupling is the reaction of a pair of the same free fatty acids creating a symmetrical hydrocarbon product, and heterocoupling is the reaction between two different free fatty acids. The mixture of fatty acids derived from the hydrolysis of a plant oil, microbial oil, animal fat, or combination thereof undergo both homo-coupling reactions and heterocoupling reactions during Kolbe electrolysis to produce a mixture of symmetrical and asymmetrical hydrocarbon products. The resulting hydrocarbons constitute a range of chain lengths and molecular weights, including those derived from disproportionation of the radical intermediates, which are in the range suitable for diesel fuel, heavy fuel oil and lubricant base oil.

The productivity of the Kolbe reaction is critical to the commercial success of producing hydrocarbons from free fatty acids. The efficiency of the use of electrical current is measured by the current yield, which is defined as the percentage of current used for the reaction of interest (Kolbe electrolysis) relative to the total current applied. For commercial use, however, the cost of electrical power is as important as the current yield, and as such the cell voltage is another critical parameter. The inventors have defined a new term, "productivity", defined herein as the product yield divided by the electrical energy required, in units such as g/kWh. By optimizing this value, a high productivity is obtained resulting in lower production costs. In the case of Kolbe electrolysis, the specified product for the calculation of productivity is defined as all the hydrocarbons of interest for a specific application derived from the substrate fatty acids.

Products of the hydrolysis reaction which can be present in the Kolbe electrolysis reaction solution may include some unreacted triglycerides, diglycerides, monoglycerides, or glycerol depending upon the feedstock. In the present invention preferably the hydrolysis reaction includes a significant aqueous phase and is designed so that all of the feedstock fats and oils are hydrolyzed into a water-insoluble free fatty acids phase which floats on top of the aqueous phase. Preferably the glycerol byproduct of the hydrolysis reaction fully dissolves into the aqueous phase. In one embodiment of the present invention, the hydrolysis is performed with a base catalyst in a C1-C3 alcohol. It may be advantageous to retain or recover the solvent and/or base from the hydrolysis reaction, for the Kolbe electrolysis reaction.

Preferred solvents for the Kolbe electrolysis include C1-C3 alcohols. More preferably the solvents employed in the Kolbe electrolysis reaction are methanol or ethanol or a mixture of C1-C3 alcohols thereof. The reaction is tolerant to the presence of water, and water may be present in this reaction in amounts up to 40% by volume. In certain embodiments, solubility of reaction components may be improved in a solvent system which comprises a mixture of alcohol and water.. More preferably the solvent system for the Kolbe reaction comprises about 2% to 50%, about 5% to 45%, about 10% to 40% or about 20% to 30% by volume (water in ethanol).

The initial reaction mixture for the Kolbe electrolysis reaction may not be a solution (with the feedstock and other components dissolved) at ambient temperature (22° C.). During the Kolbe electrolysis reaction, the neutralized (i.e., salt) form of the fatty acid must be in solution. The free fatty acid can exist as a separate phase. As the carboxylate ion form of the fatty acid is converted to hydrocarbon during electrolysis, the base, which is formed in this reaction, reacts with the free fatty acid to form a salt, thereby drawing more fatty acid (in its salt form) into solution. This continues until all the fatty acid is consumed.

In some embodiments of the present invention, the Kolbe electrolysis can be performed at temperatures below or above room temperature. Preferably the Kolbe electrolysis reaction is conducted at a temperature in the range of about 15° C. to about 100° C. Higher pressures than atmospheric pressure can be employed to prevent loss of the solvent or a boiling over of the reaction mixture. In instances where a volatile fatty acid is present following the hydrolysis reaction, in some embodiments of the present invention, the volatile fatty acid can be allowed to volatilize by lowering the pressure following or during the hydrolysis reaction in order to eliminate volatile fatty acids from being present during the Kolbe electrolysis reaction.

In the Kolbe electrolysis reaction, a base can be added to partially convert the carboxylic acid group of the fatty acids to a carboxylate salt prior to initiating or during the Kolbe reaction undergoing electrolysis. In some embodiments of the present invention preferably the fatty acids will be neutralized by ranges from about 10 to 80, 20 to 60, or 30 to 50 percent. In this case the percent means the concentration of the base in molar units relative to the total carboxylic acid molar concentration. The preferred bases for the neutralization of the fatty acids are hydroxide, alkoxide or carbonate salts of sodium or potassium. Amine bases can also be used. Anions other than the carboxylates of the substrate carboxylic acids may interfere and should not be present. In some embodiments of the present invention an electrolyte can be added to the Kolbe reaction mixture to increase the Kolbe reaction mixture electrical conductivity. Preferably an electrolyte to improve the Kolbe reaction mixture electrical conductivity is selected from the group consisting of perchlorate, p-toluenesulfonate or tetrafluoroborate salts of sodium or tetraalkylammonium or a mixture thereof. An increase in mixture conductivity corresponds with a decrease in mixture resistivity.

The preferred material of the cathode in Kolbe electrolysis is stainless steel, nickel, or graphite, although other suitable materials can also be used, including platinum or gold. The preferred material of the anode is platinum, at least at the reacting surface of the anode. The anode can be a foil or plate consisting of the preferred anode material or the anode material can be plated on or affixed to a support material such as titanium, graphite, or glass, with the preferred support material being titanium. For example, an anode consisting of a 1 mm-thick titanium plate electroplated with 1 micrometer of platinum was used for the Kolbe electrolysis of oleic acid to give a productivity value equivalent to that found using a platinum foil anode. Other materials can also be used as the anode, including non-porous graphite, gold or palladium.

The preferred current density, defined as the current supplied to the electrode divided by the active surface area of the electrode, applied to the Kolbe electrolysis is 0.05-1.0, 0.1-0.4 or 0.1-0.3 A/cm$^2$.

Figure 4:
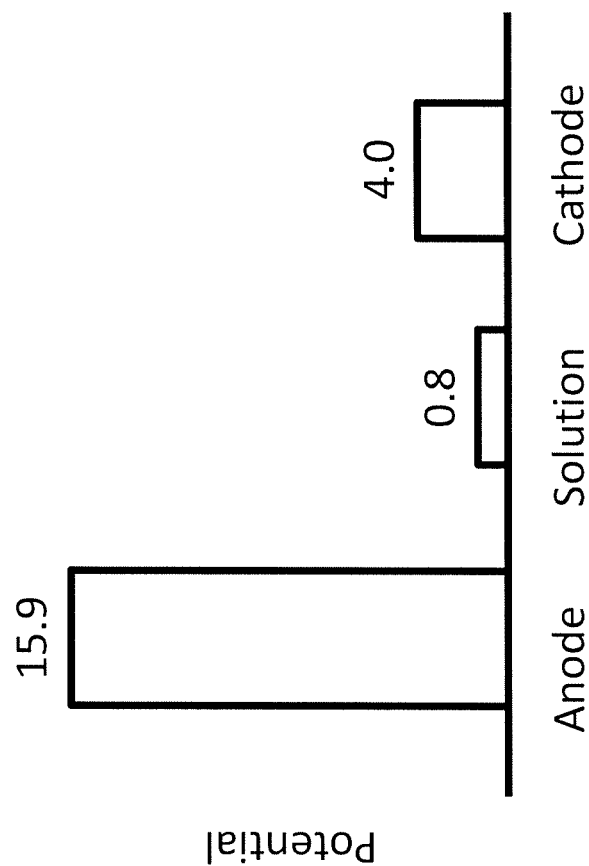
FIG. 4 depicts an example of the relative contributions of anode, solution, and cathode to the overall potential occurring during a Kolbe electrolysis reaction of oleic acid in the presence of sodium hydroxide in 70% ethanol/water by volume.

As shown in the Kolbe reaction example depicted in FIG. 4 the net (overall) cell voltage (voltage means electrical potential) of a Kolbe electrolysis reaction cell can be 20.7 volts. The overall cell voltage (also termed the net cell voltage) is a measureable cell voltage between the anode electrode and the cathode electrode. In some embodiments of the present invention as exemplified in Kolbe electrolysis reactions of Examples 1, 2, 3, 4, 5, 6, 7 and 8, the measured cell voltage is between about 12.2 volts to about 52 volts depending upon reaction conditions, which include the type of triglyceride, the amount and type of base, the electrical current density, and the reaction temperature.

This overall cell voltage (cell voltage or net cell voltage) drop measured between the immersed anode and cathode electrodes is believed to be comprised of several voltage drops occurring in the Kolbe electrolysis reaction cells. The cell voltage drop may be due to several factors. These factors in FIG. 4 for example include:
(a) an anode potential drop of 15.9 volts in the example of FIG. 4 which in part is caused by the Kolbe electrolysis reaction with fatty acids and which may change during the Kolbe reaction due to a development of an overvoltage drop on the external immersed electrode surfaces which in part may be caused by an anode electrode passivation process;
(b) a cathode potential drop of 4.0 V in the example of FIG. 4, which can change during the Kolbe reaction due to a development of an overvoltage drop on the external immersed electrode surfaces which, in part, can be caused by a cathode passivation process;
(c) a Kolbe reaction cell solution voltage drop of 0.8 volts due to solution resistivity and current flow between the electrodes (which, according the Ohm's law, can be calculated as the mathematical product of the measured solution resistance between the electrodes before the Kolbe reaction solution and the current flow between the electrodes.

The passivation process at the immersed electrodes during the Kolbe reaction is a chemical process problem which needs to be controlled when possible. Passivation can be found to be a voltage-dependent, a current-dependent, or a solution resistivity-dependent factor. The causes and means to modulate electrode passivation can require controlling many Kolbe reaction conditions, and thus controlling passivation can be problematic.

For example, in some embodiments of the present invention, the net cell voltage needs to be minimized to make the Kolbe process economical, which means not wasting the electricity going into the Kolbe electrolysis reaction. The net cell voltage is a voltage that can be current-dependent and would be cell resistivity dependent. The electrical current at an adequate electrochemical voltage driving force in the Kolbe reaction cell causes Kolbe electrolysis reaction of free fatty acids to have an adequate yield and reasonable reaction duration. For example, for some embodiments of the present invention, preferably the current flow ranges between about 0.05 to about 0.50 amperes/cm$^2$ across the conductive surfaces of the anode and cathode during the Kolbe reaction to have a reaction yield of about 95% and a reaction duration of about one hour. In the example in FIG. 4, the Kolbe cell reaction solution was a 70% ethanol-30% water solution and the fatty acid was 0.5 M oleic acid that has been neutralized by 40 mole percent with sodium hydroxide. The Kolbe electrodes had a 1.5 mm solution gap and the Kolbe reaction was operated with a current density of 0.2 amperes/cm$^2$ of electrode area.

In the present invention, passivation at the electrodes employed during the Kolbe electrolysis was considered a wasteful electrical usage problem that needed to be reduced to make commercially practicing the present invention an economically viable process for creating hydrocarbons. However, at the same time for some embodiments of the present invention, the yield of the desired Kolbe hydrocarbon product needed to be a high yield. It was found that the amount of electrode voltage passivation could be reduced by using fatty acids in the Kolbe reaction solution from sources having a fatty acid composition comprising a higher weight percent of saturated fatty acids and lower weight percent of unsaturated fatty acids.

As mentioned by the example in FIG. 4, there are multiple factors which impact the overall cell voltage of a Kolbe electrolysis reaction. The electrochemical potentials for the anodic and cathodic reactions are expected to contribute about 2.5 V and <2 V, respectively, so that the remainder of the voltage measured for the anode and cathode come from electrode passivation. Thus, in the example of FIG. 4, the anodic overvoltage constitutes the majority of the overall cell voltage of 20.7 V. Electrical resistance of the solution can be reduced by adding a supporting electrolyte to the solution, although in the example in FIG. 4 solution resistance voltage drop is not a significant contributor, accounting for only 0.55 V/millimeter (mm) electrode gap distance. In the example depicted in FIG. 4 there is only a 1.5 millimeter electrode gap which results in only 0.825 V attributable to solution resistance Electrode passivation has been found to increase as the amount of polyunsaturated fatty acids increases in the fatty acid substrate of the Kolbe reaction. For example, the present inventors have found that a substrate comprising more polyunsaturated fatty acids leads to greater passivation than a substrate comprising more mono-unsaturated fatty acids or more saturated fatty acids. A reduction in the effects of passivation, and thus cell voltage, is considered to have an important direct impact on the productivity of the reaction.

The productivity (P) for the Kolbe electrolysis of a mixture of fatty acids, in g/kW·h, can be calculated as:

$$P = M \cdot 1000/(i \cdot V \cdot t)$$

where M is the mass of products of interest generated, in grams; i is the electrical current supplied to the electrochemical cell, in amperes; V is the voltage applied to the electrochemical cell, in volts; and t is the time over which current has been supplied, in hours.

Figure 5:
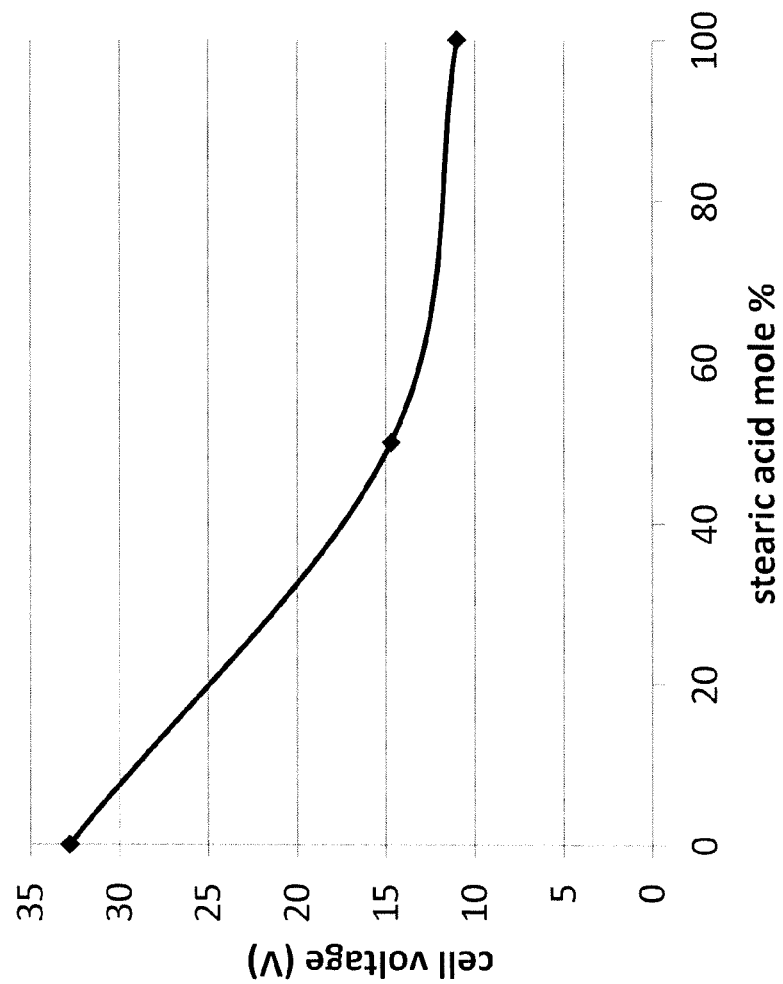
FIG. 5 depicts a graph plotting the dependence of the cell voltage of a Kolbe electrolysis reaction of oleic acid as a function of the mole percent of stearic acid added.

In one aspect of the invention, the productivity of the Kolbe electrolysis reaction is improved by adding an amount of saturated fatty acid to the reaction mixture containing a mixture of fatty acids derived from a plant oil, microbial oil, animal fat or combination thereof. FIG. 5 shows the dependence of cell voltage on the mole % stearic acid mixed with oleic acid. Similarly, the productivity of the Kolbe electrolysis reaction improves as the overall degree of saturation of the fatty acid reactants increases.

Surprisingly, this dependence is not linear. When stearic acid comprises 50% of the total fatty acids when mixed with oleic acid, the cell voltage was lowered from 32.8 V in the case of 100% oleic acid to 14.7 V, or to 45% of original. This translates to an increase in productivity of 123%. Further increase in stearic acid content from 50 to 100% stearic acid results in a much smaller decrease in cell voltage from 14.7 V to 11.0 V. This result shows that one or more fatty acids of interest that would otherwise give high cell voltage in the Kolbe electrolysis reaction can be used at much lower cell voltage with the addition of more saturated fatty acids to the reaction mixture.

In another aspect of the invention, the productivity of the Kolbe electrolysis reaction is improved by adding a fatty acid mixture obtained from the hydrolysis of a plant oil, microbial oil or animal fat, wherein the fatty acid mixture is high in saturated fatty acids and low in unsaturated fatty acids. To assess the extent of unsaturation in a particular plant oil, microbial oil or animal fat, the fatty acid compositions for an oil or fat source, such as those listed in Table 2, were used to assign a saturation score to the oil/fat. The saturation score (S) is defined as:

$$S = (2w_s + w_{mu})/(w_{mu} + 2w_{du} + 3w_{tu})$$

where $w_s$, $w_{mu}$, $w_{du}$ and $w_{tu}$ are weight percent of fatty acids that are saturated ($w_s$), and having one ($w_{mu}$), two ($w_{du}$) or three ($w_{tu}$) double bonds, respectively. The formula is designed to normalize monounsaturated fatty acids to have a saturation score of 1.0.

Figure 6:
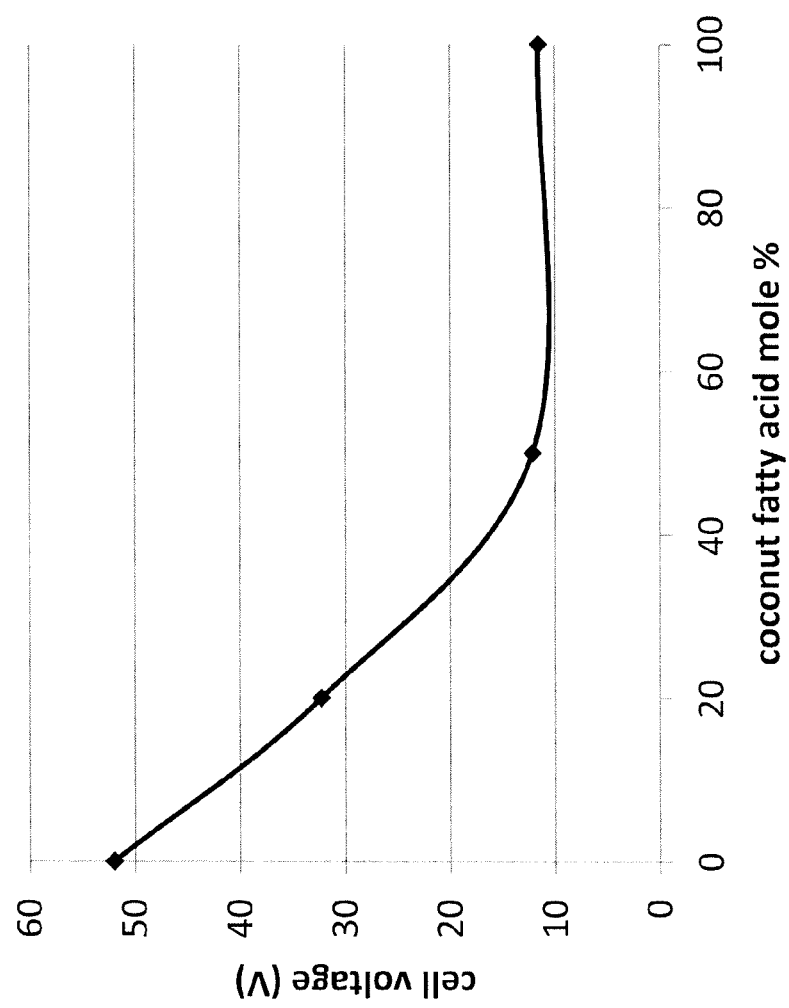
FIG. 6 depicts a graph plotting the dependence of the cell voltage of a Kolbe electrolysis reaction of soybean oil fatty acids as a function of the mole percent of coconut oil fatty acids added.
Figure 7:
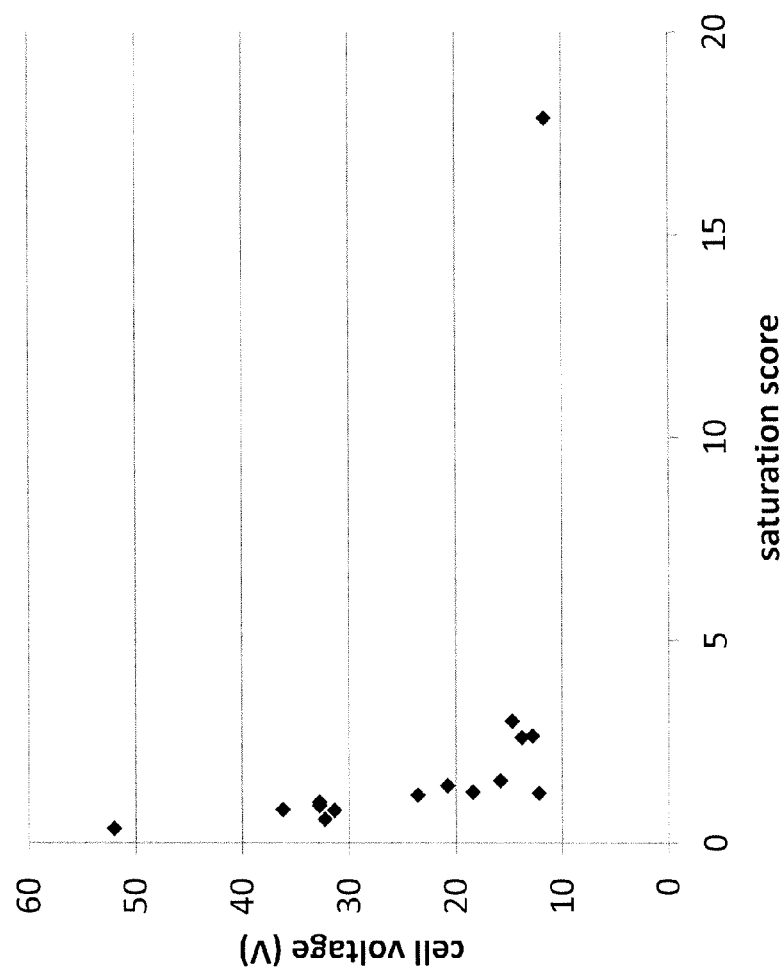
FIG. 7 depicts a graph plotting the dependence of the cell voltage on the saturation score of various mixtures of fatty acids used in a Kolbe electrolysis reaction.

Table 3 shows the saturation score of several commercially important oils and fats. A particular oil or fat can be selected based on a high saturation score, wherein the selected oil or fat can be hydrolyzed to give a mixture of fatty acids that can be added to the Kolbe reaction to improve productivity. FIG. 6 shows the dependence of cell voltage on the mole % of fatty acids derived from coconut oil (having a saturation score of 17.87) mixed with fatty acids derived from soybean oil (having a saturation score of 0.35). The relationship between fatty acid content and cell voltage is again non-linear, indicating that cell voltage was lowered from 52.0 V in the case of 100% fatty acids derived from soybean oil to 12.2 V in the case of a mixture of 50% soybean oil fatty acids and 50% coconut oil fatty acids. This drop of voltage corresponds to a 326% increase in productivity of the Kolbe reaction, which has a large impact on the operating costs of this process. In this way, an inexpensive feedstock, e.g. used cooking oil, which would otherwise cause high cell voltage in Kolbe electrolysis, can be used to produce valuable hydrocarbons when mixed with an oil or fat having a high saturation score to greatly improve the operating costs. FIG. 7 shows the correlation between the saturation score of a particular fatty acid mixture and corresponding cell voltage measured for a Kolbe electrolysis reaction of that mixture under similar conditions. At saturation scores of less than about 1.0, the cell voltage is high and there is a strong dependence of cell voltage on saturation score. Above a saturation score of about 1.2, the cell voltage is much lower and the change in cell voltage with further increases in saturation score is much less. Indeed, for pure stearic acid (having an infinite saturation score), the cell voltage is 11.0 V, very near the cell voltage of 11.6 V for coconut oil fatty acids (saturation score of 17.87). Thus, it is desirable to choose a mixture of fatty acids for which the combined saturation score is greater than 1.

TABLE 3

Saturation scores for several commercially important oils and fats*

| Oil/Fat Source | Saturation Score (S) |
|---|---|
| coconut | 17.87 |
| palm kernel | 9.11 |
| tallow | 2.60 |
| palm | 2.33 |
| lard | 2.00 |
| oleic acid | 1.00 |
| jatropha | 0.79 |
| canola | 0.54 |
| corn | 0.37 |
| soybean | 0.35 |

*the S values were calculated using the formula provide above and the known fatty acid content of the oil/fat sources.

Olefin Metathesis

In accordance with certain embodiments, the process of the present invention can include the step of olefin metathesis with ethene (i.e., ethenolysis) or other lower alkene, such as propene, to modify the chain length of the hydrocarbons and to produce linear alpha olefins. In certain embodiments, branched hydrocarbons can be produced, for example, by use of alkenes having two alkyl substituents on one double-bonded carbon, such as 2-methylpropene (isobutylene), in place of ethene in the olefin metathesis reaction. When employed, olefin metathesis can be performed prior to the hydrolysis and Kolbe electrolysis or in-between the hydrolysis and Kolbe electrolysis or, in the preferred embodiment, subsequent to Kolbe electrolysis.

Metathesis is a process involving the exchange of a bond (or bonds) between similar interacting chemical species such that the bonding affiliations in the products are closely similar or identical to those in the reactants. Olefin metathesis reactions operate specifically at carbon-carbon double bonds. In such reactions, an olefin described generically as A=A can react with a second olefin, B=B, to yield a cross-over product, A=B. If multiple unsaturated species are available, all possible combinations of cross-over products can typically be obtained, with the product ratio determined largely by the relative concentrations of the reactants. Internal olefins can be reacted with ethene to produce smaller olefins. This reaction is referred to as ethenolysis, which produces alpha olefins (compounds with terminal double bonds). In certain embodiments, ethenolysis can be performed on the hydrocarbons derived from the Kolbe electrolysis, leading to the linear alpha olefins 1-decene, 1-heptene, 1-butene and 1,4-pentadiene, among others. These linear alpha olefins are useful as precursors to polymers, detergents, and other fine chemicals. In particular, 1-decene, and to a less extent 1-heptene and 1-butene, are useful in the production of poly-alpha olefins, specifically useful for synthetic lubricants, comprising Group IV of the API classification of lubricant base oils. Alternatively, the shorter-chain hydrocarbons produced in the olefin metathesis reaction can be used as fuel, either left mixed with longer hydrocarbons to improve the cold-flow properties of the mixture of hydrocarbons or separated, e.g., by distillation, and used as a fuel with good cold-flow properties, e.g., as kerosene would be used. In certain embodiments, wherein the olefin metathesis reaction is performed on the plant oil, microbial oil, animal fat or combination thereof, the hydrocarbon product distribution following hydrolysis and Kolbe electrolysis on the mixture would be the same as that wherein the olefin metathesis reaction is performed on the hydrocarbon products of the Kolbe electrolysis reaction.

The olefin metathesis reaction requires a transition metal catalyst. The catalyst can be either heterogeneous or homogeneous with the reaction medium. Common homogeneous catalysts include metal alkylidene complexes as have been described by Schrock, Grubbs, and others. Common heterogeneous metathesis catalysts include rhenium and molybdenum oxides supported on a silica or alumina carrier.

Figure 8:
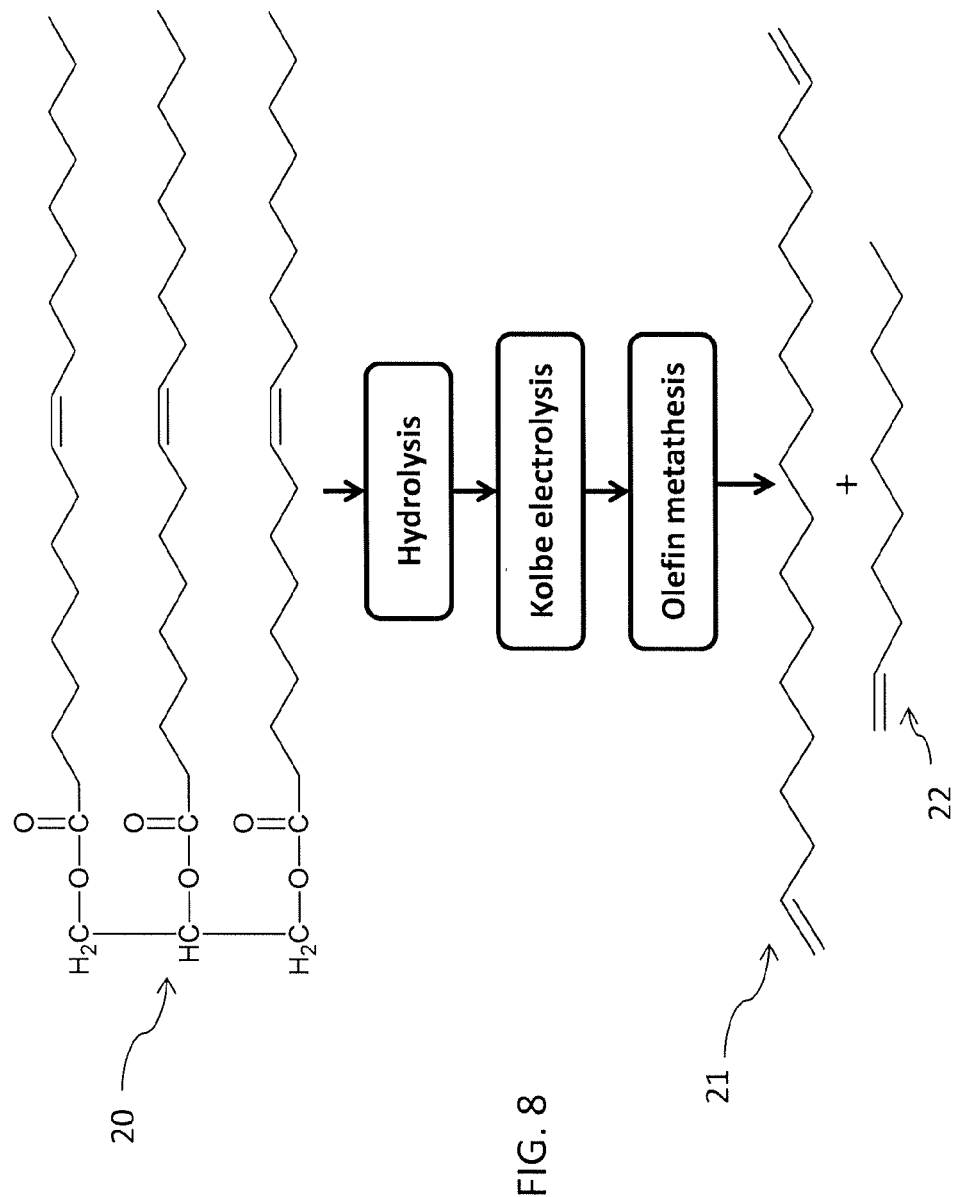
FIG. 8 depicts a series of three chemical reactions; hydrolysis, Kolbe electrolysis and olefin metathesis using as a feedstock the oil, glyceryl trioleate, to produce a mixture of two linear hydrocarbons in accordance with certain embodiments of the invention.
Figure 9:
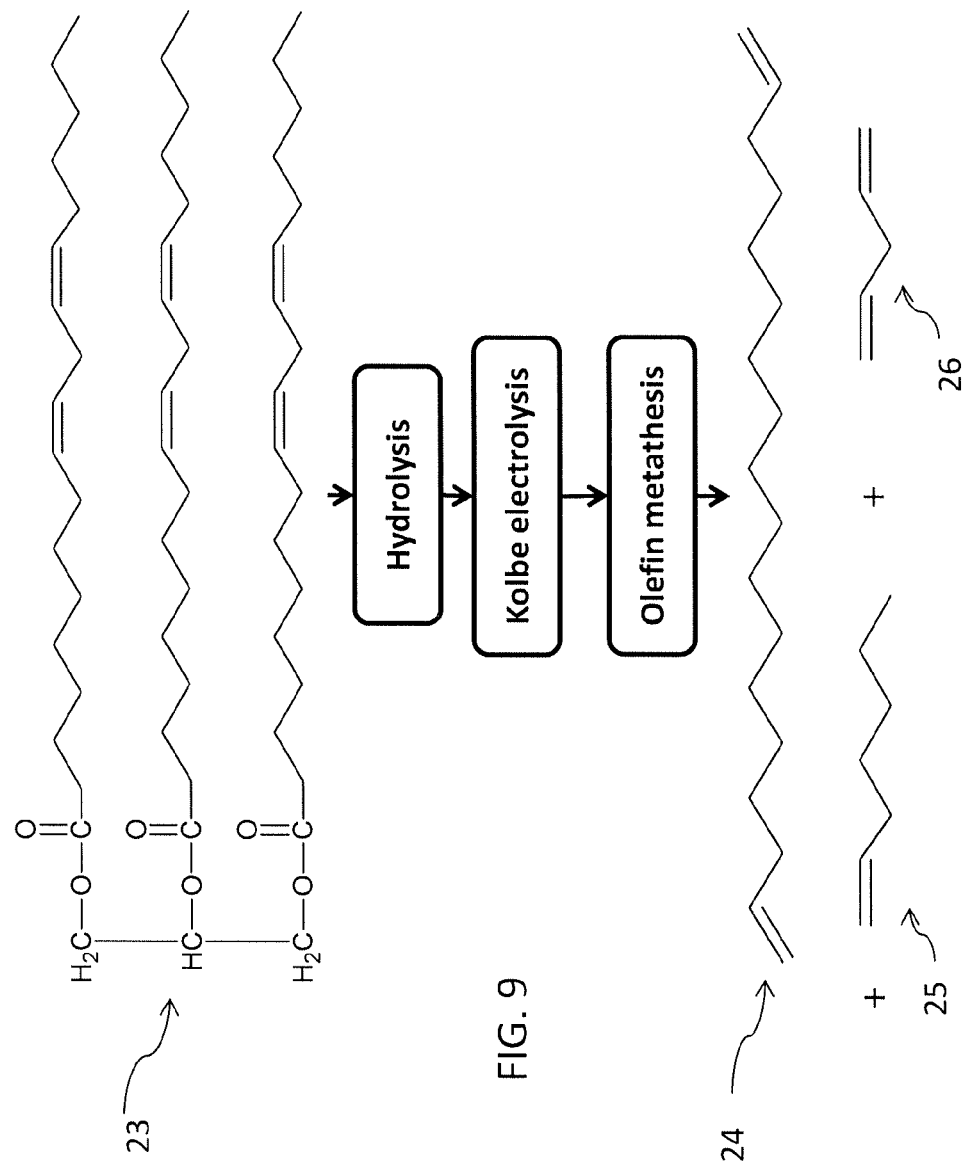
FIG. 9 depicts a series of three chemical reactions; hydrolysis, Kolbe electrolysis and olefin metathesis using as a feedstock the oil, glyceryl trilinoleate, to produce a mixture of three linear hydrocarbons in accordance with certain embodiments of the invention.

FIG. 8 and FIG. 9 show a process for producing hydrocarbon fuel from hydrocarbons produced by Kolbe electrolysis in accordance with certain embodiments of the invention. As shown in FIG. 8, glyceryl trioleate 20 (a triglyceride) is subjected to hydrolysis, Kolbe electrolysis, and olefin metathesis (ethenolysis) to produce the linear alpha olefins 1,17-octadecadiene 21, and 1-decene 22. As shown in FIG. 9, glyceryl trilinoleate 23 is subjected to hydrolysis, Kolbe electrolysis, and olefin metathesis (ethenolysis) to produce the linear alpha olefins 1,17-octadecadiene 24, 1-heptene 25 and 1,4-pentadiene 26. The composition of linear alpha olefins derived from the olefin metathesis of hydrocarbons derived from natural oils and fats can be predicted by the average composition of fatty acids in the oil or fat as shown in Table 2, as the narrow range of fatty acids leads to a narrow range of possible linear alpha olefins. Therefore, the yield of particular desired linear alpha olefins can be improved by careful selection of plant oil, microbial oil, animal fat or combinations thereof wherein the fatty acids that lead to the desired linear alpha olefin are present in high concentration.

Hydroisomerization

In accordance with certain embodiments of the invention, hydroisomerization can be performed on the hydrocarbon product of the Kolbe electrolysis reaction to modify the properties of the hydrocarbon such that it is more suitable for use as lubricant base oil. The hydroisomerization reaction is performed in the presence of hydrogen gas and a catalyst having a metal component to catalyze skeletal isomerization, yielding saturated, branched hydrocarbons having the same molecular weight as the substrate hydrocarbons. The resulting hydrocarbon material is more stable to oxidation and is more fluid at lower temperatures, which are desirable properties. In a preferred hydroisomerization reaction process of the present invention, the catalyst is a silica-alumina zeolite containing impregnated platinum, the temperature is 250-400° C., the pressure is 10-400 bar, and the $H_2$:hydrocarbon ratio is 2-50. To gain a better understanding of the invention described herein, the following examples are set forth. It should be understood that these examples are for illustrative purposes only. Therefore, they should not limit the scope of this invention in any way.

EXAMPLES

Example 1

Kolbe Electrolysis Reaction of Beef Tallow-Derived Fatty Acids 9.44 parts fatty acids derived from the hydrolysis of beef tallow was added to 89.69 parts methanol; 0.87 parts potassium hydroxide was added to the mixture, which was then heated to 52° C. in a water jacketed vessel, obtaining a clear solution. An electrolysis cell, consisting of platinum foil anode and nickel cathode separated by 1.5 mm gap, was immersed into the solution. A constant electrical current density of 0.2 A $cm^{-2}$ was applied. Within 1 hour, hydrocarbon product separated from the reaction mixture and accumulated at the bottom of the reactor, comprising coupled Kolbe electrolysis products and disproportionation products.

Example 2

Kolbe Electrolysis Reaction of Oleic Fatty Acid in the Presence of Equimolar Stearic Acid 8.0 parts oleic acid, 8.0 parts stearic acid (50 mole % of total acid), and 0.90 parts sodium hydroxide was combined with 56.9 parts ethanol and 26.2 parts water, which was then heated to 62° C. in a water-jacketed vessel, obtaining a clear solution. An electrolysis cell, consisting of platinum foil anode and platinum foil cathode separated by 1.5 mm gap, was immersed into the solution. A constant electrical current density of 0.2 A $cm^{-2}$ was applied. Within 1 hour, hydrocarbon product separated from the reaction mixture and accumulated at the top of the reactor, comprising coupled Kolbe electrolysis products and disproportionation products.

Example 3

Kolbe Electrolysis Reaction of Oleic Fatty Acid at a Moderate Electrical Current Density 16.26 parts oleic acid and 1.15 parts sodium hydroxide was dissolved in 53.52 parts ethanol and 29.07 parts water, which was then heated to 50° C. in a water-jacketed vessel. An electrolysis cell, consisting of platinum foil anode and platinum foil cathode separated by 1.5 mm gap, was immersed into the solution. A constant electrical current density of 0.1 A $cm^{-2}$ was applied. After 100 minutes of electrolysis an aliquot of the reaction mixture was acidified and extracted into hexane, which was then analyzed by gas chromatography to calculate current yield and productivity (see Table 4).

Example 4

Kolbe Electrolysis Reaction of Oleic Fatty Acid at a High Electrical Current Density The solution of Example 4 was electrolyzed in the same manner as in Example 3, except that the current density was 0.3 A $cm^{-2}$ and the reaction time was 33.3 minutes.

Example 5

Kolbe Electrolysis of Oleic Fatty Acid 16.32 parts oleic acid and 0.97 parts sodium hydroxide was dissolved in 53.60 parts ethanol and 29.11 parts water, which was then electrolyzed in the same manner as the solution in Example 2 and analyzed in the same manner as in Example 3.

Example 6

Kolbe Electrolysis of More Neutralized Oleic Fatty Acid 16.19 parts oleic acid and 2.25 parts sodium hydroxide was dissolved in 52.85 parts ethanol and 28.71 parts water, which was then electrolyzed and analyzed in the same manner as the solution in Example 5.

Example 7

Kolbe Electrolysis of Soybean Oil Fatty Acids 15.1 parts soybean oil fatty acids and 0.90 parts sodium hydroxide was combined with 57.5 parts ethanol and 26.5 parts water, which was then heated to 60° C. in a water-jacketed vessel, obtaining a clear solution, which was then electrolyzed in the same manner as the solution in Example 2. After 60 minutes of electrolysis an aliquot of the reaction mixture was titrated with potassium hydroxide (aqueous) in 95% ethanol/5% water (by volume) using a colourimetric pH indicator, the results of which were compared to the results of a similar titration before the reaction to calculate the current yield and productivity by loss of fatty acid substrate during the reaction (see Table 4).

Example 8

Kolbe Electrolysis of Soybean Oil Fatty Acids in the Presence of Equimolar Coconut Oil Fatty Acids 8.2 parts soybean oil fatty acids, 5.2 parts coconut oil fatty acids (50 mole % of total acid), and 0.9 parts sodium hydroxide was combined with 58.6 parts ethanol and 27.0 parts water, which was then heated to 60° C. in a water-jacketed vessel, obtaining a clear solution, which was then electrolyzed and analyzed in the same manner as the solution in Example 2.

Example 9

Kolbe Electrolysis of Canola Oil Fatty Acids 10.1 parts canola oil fatty acids and 0.92 parts potassium hydroxide was combined with 95.0 parts methanol, which was then heated to 50° C. in a water jacketed vessel, obtaining a clear solution, which was then electrolyzed in the same manner as the solution in Example 2. After 5 minutes of electrolysis voltage exceeded the 40 V capacity of power supply indicating a very high degree of passivation on the anode.

Example 10

Kolbe Electrolysis of Canola Oil Fatty Acids in the Presence of Equimolar Coconut Oil Fatty Acids 5.0 parts canola oil fatty acids, 3.2 parts coconut oil fatty acids (50 mole % of total acid), and 0.9 parts potassium hydroxide was combined with 95.0 parts methanol, which was then heated to 50° C. in a water jacketed vessel, obtaining a clear solution, which was then electrolyzed in the same manner as the solution in Example 2, and analyzed in the same manner as the solution in Example 7.

As disclosed in the above Examples and summarized in Table 4 data for the Examples, the Kolbe electrolysis reaction of oleic acid under various conditions is associated with moderate productivity in the range of 170.9-252.5 g/kWh. The saturation score for pure oleic acid is 1.00 (see Table 3). Comparing this productivity with that from Example 7, which describes the Kolbe electrolysis of soybean oil fatty acids under otherwise similar conditions, the cell voltage in the case of the soy fatty acids was much higher, leading to a much lower productivity of 102.4. The saturation score for soy fatty acids (see Table 3) is only 0.35, explaining the high cell voltage caused by intense electrode passivation. Comparing the productivity from Example 7 with that from Example 8 demonstrates the value of selecting fatty acids from a combination of sources based on the saturation score associated with those sources. The productivity associated with Example 8 is much higher (370.7 g/kWh) than that associated with Example 7, which is a direct result of adding fatty acids derived from coconut oil, which has a saturation score of 17.87. The inclusion of the coconut oil fatty acids caused a large decrease in cell voltage as a result of much reduced electrode passivation.

The results of Example 8 with soy and coconut oil fatty acids versus the results of Example 7 with only soy fatty acids are surprising as the relationship between cell voltage (and hence productivity) and fatty acid mixing ratio is non-linear and unknown in the prior art. Further addition of fatty acids derived from an oil or fat with a high saturation score, such as coconut oil, would not significantly affect the cell voltage beyond about 50 mole % of the total fatty acids, as shown in FIG. 6. Thus, the careful selection of sources of fatty acids based on saturation score allows a significant operating cost savings for the Kolbe electrolysis of fatty acids by greatly reducing the electrode passivation that arises during the reaction, and hence the cell voltage necessary to perform the reaction. Further cost savings are realized when a less expensive fatty acid source having a low saturation score is used in combination with a fatty acid source having a high saturation score, as cell voltage can be greatly reduced by mixing only about 50 mole % or less of the fatty acids from the source having a high saturation score.

The results of Example 10, from Kolbe electrolysis of a 50:50 (mole percent) mix of canola oil and coconut oil, in comparison with the results of Example 9, from Kolbe electrolysis of 100% canola oil, further demonstrate the advantage associated with addition of fatty acids derived from an oil or fat with a high saturation score. In this case, the results demonstrated a dramatic improvement in productivity.

TABLE 4

Current yield and productivity data for experiments described in Examples 3-10

|  | Current yield (%) | Cell voltage (V) | Productivity (g/kWh) |
|---|---|---|---|
| Example 3 | 66.7 | 24.2 | 244.7 |
| Example 4 | 61.7 | 32.0 | 170.9 |
| Example 5 | 79.5 | 27.9 | 252.5 |
| Example 6 | 29.0 | 12.5 | 206.4 |
| Example 7 | 61.2 | 52.0 | 102.4 |
| Example 8 | 60.9 | 12.2 | 370.7 |
| Example 9 | ~60-70 | >40.0 | <260 |
| Example 10 | 64.3 | 12.5 | 461.6 |

Example 11

Ethenolysis of Oleic Acid-Derived Kolbe Reaction Products in Dichloromethane, an Olefin Metathesis Process 3.00 parts hydrocarbons from the Kolbe electrolysis of oleic acid were added to a vessel; 0.62 parts catalyst (commercial Grubbs' $2^{nd}$ generation metathesis catalyst) was dissolved in 96.38 parts dichloromethane and the resulting solution was added to the vessel. The vessel was sealed and pressurized with ethene to 52 bar. The reaction was stirred at ambient temperature for 2 hours, at which time the vessel was depressurized and ethyl vinyl ether was added to quench the reaction. The contents were passed through silica and analyzed by GC-MS. Results confirmed that 1-decene and 1,17-octadecadiene, the only linear alpha olefins expected from a substrate derived entirely from oleic acid, were the only ethenolysis products present in the reaction mixture.

Example 12

Hydroisomerization of a Straight Chain Hydrocarbon Product of a Kolbe Electrolysis Reaction to Add Side-Chains to the Straight Chain Hydrocarbon Thereby Reducing its Pour Point The product from the Kolbe electrolysis of a fatty acid mixture was subjected to vacuum distillation to remove hydrocarbons with atmospheric boiling points <250° C. The residue was passed through a fixed bed reactor containing a catalyst comprising an acidic, porous silica-alumina support and 0.5 weight percent platinum loaded onto the support by incipient wetness impregnation. The reactor was heated to 300° C. and pressurized with hydrogen gas to 50 bar. The liquid hourly space velocity was 1 $h^{-1}$ and the hydrogen: substrate feed ratio was 10:1. The pour point of this material was reduced from 40+° C. to −12° C.

In one embodiment there is provided a method of increasing productivity of a Kolbe electrolysis reaction forming one or more C6 to C54 hydrocarbons, the method comprising:

combining one or more C4-C28 unsaturated fatty acids with a solvent to create a reaction mixture; adding one or more C4-C28 saturated fatty acid; and performing a Kolbe electrolysis reaction on the combined reaction mixture to produce one or more C6 to C54 hydrocarbons, wherein the saturated fatty acids are selected to lower a passivation voltage of an electrode used in the Kolbe electrolysis reaction.

In another embodiment, the invention is method of increasing productivity of a Kolbe electrolysis reaction forming one or more C6 to C54 hydrocarbons, the method comprising: combining one or more C4-C28 unsaturated fatty acids with a solvent to create a reaction mixture; adding one or more C4-C28 saturated fatty acids; and performing a Kolbe electrolysis reaction on the combined reaction mixture to produce one or more C6 to C54 hydrocarbons, wherein the saturated fatty acids are selected to lower a passivation voltage of an electrode used in the Kolbe electrolysis reaction, and wherein the saturation score of the combined reaction mixture is greater than about 1.0, is greater than about 1.2 (or approximatelyl.2), is greater than about 1.3, is greater than about 1.4 , is greater than about 1.5, is greater than about 1.6, is greater than about 1.7, is greater than about 2.0, is greater than about 3.0, is greater than about 5, is greater than about 10, or is greater than about 15.

In another embodiment, the invention is a method of increasing productivity of a Kolbe electrolysis reaction forming one or more C6 to C54 hydrocarbons, the method comprising: combining one or more C4-C28 unsaturated fatty acids with a solvent to create a reaction mixture; adding one or more C4-C28 saturated fatty acids ; and performing a Kolbe electrolysis reaction on the combined reaction mixture to produce one or more C6 to C54 hydrocarbons, wherein the saturated fatty acids are selected to lower a passivation voltage of an electrode used in the Kolbe electrolysis reaction, and wherein the solvent is selected from the group consisting of a Cl to C4 alcohol, methanol, ethanol, propanol, isopropanol, butanol, water, and a mixture thereof, and wherein the solvent is a mixture which contains between about 0.5 percent to about 50 percent water by volume.

In another embodiment, the invention is a method of increasing productivity of a Kolbe electrolysis reaction forming one or more C6 to C54 hydrocarbons, the method comprising: combining one or more C4-C28 unsaturated fatty acids with a solvent to create a reaction mixture; adding one or more C4-C28 saturated fatty acids ; and performing a Kolbe electrolysis reaction on the combined reaction mixture to produce one or more C6 to C54 hydrocarbons, wherein the saturated fatty acids are selected to lower a passivation voltage of an electrode used in the Kolbe electrolysis reaction, and wherein the reaction mixture for the Kolbe electrolysis reaction is not a solution at room temperature, or the reaction mixture for the Kolbe electrolysis reaction is partially a solution at room temperature, or the reaction mixture for the Kolbe electrolysis reaction is a solution at room temperature.

In another embodiment, the invention is a method of increasing productivity of a Kolbe electrolysis reaction forming one or more C6 to C54 hydrocarbons, the method comprising: combining one or more C4-C28 unsaturated fatty acids with a solvent to create a reaction mixture; adding one or more C4-C28 saturated fatty acids; and performing a Kolbe electrolysis reaction on the combined reaction mixture to produce one or more C6 to C54 hydrocarbons, wherein the saturated fatty acids are selected to lower a passivation voltage of an electrode used in the Kolbe electrolysis reaction, and wherein the one or more C4-C28 fatty acids in the solvent are reacted with a base to form an amount of a salt of the one or more C4-C28 fatty acids.

In another embodiment, the invention is a method of increasing productivity of a Kolbe electrolysis reaction forming one or more C6 to C54 hydrocarbons, the method comprising: combining one or more C4-C28 unsaturated fatty acids with a solvent to create a reaction mixture; adding one or more C4-C28 saturated fatty acids ; and performing a Kolbe electrolysis reaction on the combined reaction mixture to produce one or more C6 to C54 hydrocarbons, wherein the saturated fatty acids are selected to lower a passivation voltage of an electrode used in the Kolbe electrolysis reaction, and wherein an electrolyte is added to the reaction mixture to improve electrical conductivity of the Kolbe electrolysis reaction, and wherein the electrolyte is selected from the group consisting of a perchlorate salt, a p-toluenesulfonate salt, a tetrafluoroborate salt, and mixtures thereof.

In another embodiment, the invention is a method of increasing productivity of a Kolbe electrolysis reaction forming one or more C6 to C54 hydrocarbons, the method comprising: combining one or more C4-C28 unsaturated fatty acids with a solvent to create a reaction mixture; adding one or more C4-C28 saturated fatty acids ; and performing a Kolbe electrolysis reaction on the combined reaction mixture to produce one or more C6 to C54 hydrocarbons, wherein the saturated fatty acids are selected to lower a passivation voltage of an electrode used in the Kolbe electrolysis reaction, and wherein the Kolbe electrolysis reaction is conducted at a temperature in a range of about 15° C. to about 100° C.

In another embodiment, the invention is a method of increasing productivity of a Kolbe electrolysis reaction forming one or more C6 to C54 hydrocarbons, the method comprising: combining one or more C4-C28 unsaturated fatty acids with a solvent to create a reaction mixture; adding one or more C4-C28 saturated fatty acids ; and performing a Kolbe electrolysis reaction on the combined reaction mixture to produce one or more C6 to C54 hydrocarbons, wherein the saturated fatty acids are selected to lower a passivation voltage of an electrode used in the Kolbe electrolysis reaction, and wherein a pressure is imposed on the reaction mixture during the Kolbe electrolysis reaction to change a rate of loss of the solvent or to change a rate of loss of a volatile fatty acid.

In another embodiment, the invention is a method of increasing productivity of a Kolbe electrolysis reaction forming one or more C6 to C54 hydrocarbons, the method comprising: combining one or more C4-C28 unsaturated fatty acids with a solvent to create a reaction mixture; adding one or more C4-C28 saturated fatty acids ; and performing a Kolbe electrolysis reaction on the combined reaction mixture to produce one or more C6 to C54 hydrocarbons, wherein the saturated fatty acids are selected to lower a passivation voltage of an electrode used in the Kolbe electrolysis reaction, and wherein an electrical current supplied to electrodes is between about 0.05-1.0 amperes per $cm^2$ area of the electrodes.

In another embodiment, the invention is a method of increasing productivity of a Kolbe electrolysis reaction forming one or more C6 to C54 hydrocarbons, the method comprising: combining one or more C4-C28 unsaturated fatty acids with a solvent to create a reaction mixture; adding one or more C4-C28 saturated fatty acids ; and performing a Kolbe electrolysis reaction on the combined reaction mixture to produce one or more C6 to C54 hydrocarbons, wherein the saturated fatty acids are selected to lower a passivation voltage of an electrode used in the Kolbe electrolysis reaction, and wherein the reacting surface of an anode electrode is a platinum group metal, which includes platinum, iridium, palladium, ruthenium, rhodium, and osmium; or a carbon material, which includes graphite, glassy carbon, baked carbon; or is a mixture of the platinum group metal and the carbon material.

In another embodiment, the invention is a method of increasing productivity of a Kolbe electrolysis reaction forming one or more C6 to C54 hydrocarbons, the method comprising: combining one or more C4-C28 unsaturated fatty acids with a solvent to create a reaction mixture; adding one or more C4-C28 saturated fatty acids ; and performing a Kolbe electrolysis reaction on the combined reaction mixture to produce one or more C6 to C54 hydrocarbons, wherein the saturated fatty acids are selected to lower a passivation voltage of an electrode used in the Kolbe electrolysis reaction, and further comprises: following the Kolbe electrolysis reaction with an olefin metathesis reaction using a C2-C5 aliphatic alkene or a mixture of C2-C5 aliphatic alkenes, wherein the olefin metathesis reaction modifies a chain length of the hydrocarbon.

In another embodiment, the invention is a method of increasing productivity of a Kolbe electrolysis reaction forming one or more C6 to C54 hydrocarbons, the method comprising: combining one or more C4-C28 unsaturated fatty acids with a solvent to create a reaction mixture; adding one or more C4-C28 saturated fatty acids; and performing a Kolbe electrolysis reaction on the combined reaction mixture to produce one or more C6 to C54 hydrocarbons, wherein the saturated fatty acids are selected to lower a passivation voltage of an electrode used in the Kolbe electrolysis reaction, and further comprises following the Kolbe electrolysis reaction with an ethenolysis reaction using ethene to obtain 1-decene, 1-heptene, 1-butene, 1-octene, 1-hexene, or 1,4-pentadiene.

In another embodiment, the invention is a method of increasing productivity of a Kolbe electrolysis reaction forming one or more C6 to C54 hydrocarbons, the method comprising: combining one or more C4-C28 unsaturated fatty acids with a solvent to create a reaction mixture; adding one or more C4-C28 saturated fatty acids ; and performing a Kolbe electrolysis reaction on the combined reaction mixture to produce one or more C6 to C54 hydrocarbons, wherein the saturated fatty acids are selected to lower a passivation voltage of an electrode used in the Kolbe electrolysis reaction, and further comprises following the Kolbe electrolysis reaction with an ethenolysis reaction using ethene to obtain 1-decene, 1-heptene, 1-butene, 1-octene, 1-hexene, or 1,4-pentadiene, and further comprises separating the products of the ethenolysis reaction to obtain 1-decene, 1-heptene, 1-butene, 1-octene, 1-hexene, 1,4-pentadiene, a diesel fuel, and a heavy fuel oil.

In another embodiment, the invention is a method of increasing productivity of a Kolbe electrolysis reaction forming one or more C6 to C54 hydrocarbons, the method comprising: combining one or more C4-C28 unsaturated fatty acids with a solvent to create a reaction mixture; adding one or more C4-C28 saturated fatty acids ; and performing a Kolbe electrolysis reaction on the combined reaction mixture to produce one or more C6 to C54 hydrocarbons, wherein the saturated fatty acids are selected to lower a passivation voltage of an electrode used in the Kolbe electrolysis reaction, and further comprises hydroisomerizing at least some of the products from the Kolbe electrolysis reaction to produce a lubricant base oil.

In another embodiment, the invention is a method of increasing productivity of a Kolbe electrolysis reaction forming one or more C6 to C54 hydrocarbons, the method comprising: combining one or more C4-C28 unsaturated fatty acids with a solvent to create a reaction mixture; adding one or more C4-C28 saturated fatty acids ; and performing a Kolbe electrolysis reaction on the combined reaction mixture to produce one or more C6 to C54 hydrocarbons; wherein the saturated fatty acids are selected to lower a passivation voltage of an electrode used in the Kolbe electrolysis reaction, and further comprises hydroisomerizing at least some of the products from the Kolbe electrolysis reaction to produce a lubricant base oil, wherein the hydroisomerization reaction uses a catalyst which is a silica/alumina-based zeolite containing impregnated platinum, a reaction temperature between about 250° C. to about 400° C., a reaction pressure between about 10 bar to about 400 bar, and a hydrogen gas to a hydrocarbon ratio between about 2 to about 50.

In another embodiment, the invention is a method of increasing productivity of a Kolbe electrolysis reaction forming one or more C6 to C54 hydrocarbons, the method comprising: combining one or more C4-C28 unsaturated fatty acids with a solvent to create a reaction mixture; adding one or more C4-C28 saturated fatty acids ; and performing a Kolbe electrolysis reaction on the combined reaction mixture to produce one or more C6 to C54 hydrocarbons, wherein the saturated fatty acids are selected to lower a passivation voltage of an electrode used in the Kolbe electrolysis reaction, and wherein the reaction mixture uses a solvent and a base from a preceding hydrolysis reaction of a triglyceride.

In another embodiment, the invention is a method of increasing productivity of a Kolbe electrolysis reaction forming one or more C6 to C54 hydrocarbons, the method comprising: combining one or more C4-C28 unsaturated fatty acids with a solvent to create a reaction mixture; adding one or more C4-C28 saturated fatty acids ; and performing a Kolbe electrolysis reaction on the combined reaction mixture to produce one or more C6 to C54 hydrocarbons, wherein the saturated fatty acids are selected to lower a passivation voltage of an electrode used in the Kolbe electrolysis reaction, and wherein the concentration of the C4-C28 fatty acid in the Kolbe electrolysis reaction is between about 0.01 molar to about 1 molar.

In another embodiment, the invention is a method of increasing productivity of a Kolbe electrolysis reaction forming one or more C6 to C54 hydrocarbons, the method comprising: combining one or more C4-C28 unsaturated fatty acids with a solvent to create a reaction mixture; adding one or more C4-C28 saturated fatty acids ; and performing a Kolbe electrolysis reaction on the combined reaction mixture to produce one or more C6 to C54 hydrocarbons, wherein the saturated fatty acids are selected to lower a passivation voltage of an electrode used in the Kolbe electrolysis reaction, and wherein the solvent is methanol.

In another embodiment, the invention is a method of increasing productivity of a Kolbe electrolysis reaction forming one or more C6 to C54 hydrocarbons, the method comprising: combining one or more C4-C28 unsaturated fatty acids with a solvent to create a reaction mixture; adding one or more C4-C28 saturated fatty acids ; and performing a Kolbe electrolysis reaction on the combined reaction mixture to produce one or more C6 to C54 hydrocarbons, wherein the saturated fatty acids are selected to lower a passivation voltage of an electrode used in the Kolbe electrolysis reaction, and wherein the solvent is ethanol.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

Whereas particular embodiments of the invention have been described herein for purposes of illustration, it will be evident to those skilled in the art that numerous variations of the details may be made without departing from the invention as set forth in the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods, constructs and materials are now described. All publications mentioned herein are incorporated herein by reference in their entirety. Where there are discrepancies in terms and definitions used in references that are incorporated by reference, the terms used in this application shall have the definitions given herein.

Where a term is provided in the singular, the inventors also contemplate aspects of the invention described by the plural of that term. As used in this specification and in the appended claims, the singular forms "a", "an" and "the" include plural references unless the context clearly dictates otherwise, e.g., "a tip" includes a plurality of tips. Thus, for example, a reference to "a method" includes one or more methods, and/or steps of the type described herein and/or which will become apparent to those persons skilled in the art upon reading this disclosure.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A method of producing C6-C54 hydrocarbons comprising:
   (a) combining one or more C4-C28 unsaturated fatty acids and one or more C4-C28 saturated fatty acids with a solvent; and
   (b) performing a Kolbe electrolysis reaction on the combined reaction mixture prepared in (a) to produce one or more C6 to C54 hydrocarbons,
   wherein the combined reaction mixture of the unsaturated and saturated fatty acids has a combined saturation score (S) of greater than 1.0, where:

$$S=(2w_s+w_{mu})/(w_{mu}+2w_{du}+3w_{tu})$$

and $w_s$, $w_{mu}$, $w_{du}$ and $w_{tu}$ are weight percent of fatty acids that are saturated ($w_s$), and having one ($w_{mu}$), two ($w_{du}$) or three ($w_{tu}$) double bonds, respectively.

2. The method of claim 1, wherein the saturation score of the combined reaction mixture is greater than approximately 1.2.

3. The method of claim 1, wherein:
   (a) the solvent is selected from the group consisting of methanol, ethanol, propanol, isopropanol, butanol, water, and a mixture thereof, and wherein the solvent is a mixture which contains between about 0.5 percent to about 50 percent water by volume;
   (b) the reaction mixture for the Kolbe electrolysis reaction is not a solution at room temperature;
   (c) the one or more C4-C28 fatty acids in the solvent are reacted with a base to form an amount of a salt of the one or more C4-C28 fatty acids;
   (d) the Kolbe electrolysis reaction is conducted at a temperature in a range of about 15° C. to about 100° C.;
   (e) the Kolbe electrolysis reaction is performed under a pressure greater than atmospheric pressure to reduce a rate of loss of the solvent or to reduce a rate of loss of a volatile fatty acid;
   (f) the combined reaction mixture comprises a solvent and a base from a preceding hydrolysis reaction of a triglyceride; and/or
   (g) an electrical current supplied to electrodes used in the Kolbe electrolysis reaction is 0.05-1.0 amperes per cm$^2$ area of the electrodes.

4. The method of claim 1, wherein an electrolyte is added to the reaction mixture to improve electrical conductivity of the Kolbe electrolysis reaction, and wherein the electrolyte is selected from the group consisting of a perchlorate salt, a p-toluenesulfonate salt, a tetrafluoroborate salt, and mixtures thereof.

5. The method of claim 1, wherein the reacting surface of an anode electrode used in the Kolbe electrolysis reaction is a platinum group metal, which includes platinum, iridium, palladium, ruthenium, rhodium, and osmium; or a carbon material, which includes graphite, glassy carbon, baked carbon; or mixture of the platinum group metal and the carbon material.

6. The method of claim 1, further comprising:
   performing an olefin metathesis reaction on a hydrocarbon product of the Kolbe electrolysis reaction using a C2-C5 aliphatic alkene or a mixture of C2-C5 aliphatic alkenes, wherein the olefin metathesis reaction modifies a chain length of the hydrocarbon product.

7. The method of claim 1, further comprising:
   performing an ethenolysis reaction on a hydrocarbon product of the Kolbe electrolysis reaction using ethene to obtain 1-decene, 1-heptene, 1-butene, 1-octene, 1-hexene, or 1,4-pentadiene.

8. The method of claim 7, further comprising:
   separating the products of the ethenolysis reaction to obtain 1-decene, 1-heptene, 1-butene, 1-octene, 1-hexene, 1,4-pentadiene, a diesel fuel, and/or a heavy fuel oil.

9. The method of claim 1, further comprising:
   hydroisomerizing at least some of the products from the Kolbe electrolysis reaction to produce, a lubricant base oil, diesel fuels, jet fuel or gasoline-type products.

10. The method of claim 9, wherein the hydroisomerization reaction uses a catalyst which is a silica/alumina-based zeolite containing impregnated platinum, a reaction temperature between about 250° C. to about 400° C., a reaction pressure between about 10 bar to about 400 bar, and a hydrogen gas to a hydrocarbon ratio between about 2 to about 50.

11. A method of increasing productivity of a Kolbe electrolysis reaction forming one or more C6 to C54 hydrocarbons, the method comprising:
   (a) combining one or more C4-C28 unsaturated fatty acids with a solvent to create a reaction mixture;
   (b) adding one or more C4-C28 saturated fatty acids to the reaction mixture; and (c) performing a Kolbe electrolysis reaction on the combined reaction mixture to produce one or more C6 to C54 hydrocarbons, wherein the saturated fatty acids are added to lower a passivation voltage of an electrode used in the Kolbe electrolysis reaction, and wherein the combined reaction mixture has a combined saturation score (S) of greater than 1.0, where:

$$S=(2w_s+w_{mu})/(w_{mu}+2w_{du}+3w_{tu})$$

and $w_s$, $w_{mu}$, $w_{du}$ and $w_{tu}$ are weight percent of fatty acids that are saturated ($w_s$), and having one ($w_{mu}$), two ($w_{du}$) or three ($w_{tu}$) double bonds, respectively.

12. The method of claim 11, wherein the saturation score of the combined reaction mixture is greater than approximately 1.2.

13. The method of claim 11, wherein:
(a) the solvent is selected from the group consisting of methanol, ethanol, propanol, isopropanol, butanol, water, and a mixture thereof, and wherein the solvent is a mixture which contains between about 0.5 percent to about 50 percent water by volume;
(b) the reaction mixture for the Kolbe electrolysis reaction is not a solution at room temperature;
(c) the one or more C4-C28 fatty acids in the solvent are reacted with a base to form an amount of a salt of the one or more C4-C28 fatty acids;
(d) the Kolbe electrolysis reaction is conducted at a temperature in a range of about 15° C. to about 100° C.;
(e) the Kolbe electrolysis reaction is performed under a pressure greater than atmospheric pressure to reduce a rate of loss of the solvent or to reduce a rate of loss of a volatile fatty acid;
(f) the combined reaction mixture comprises a solvent and a base from a preceding hydrolysis reaction of a triglyceride; and/or
(g) an electrical current supplied to electrodes used in the Kolbe electrolysis reaction is 0.05-1.0 amperes per cm$^2$ area of the electrodes.

14. The method of claim 11, wherein an electrolyte is added to the reaction mixture to improve electrical conductivity of the Kolbe electrolysis reaction, and wherein the electrolyte is selected from the group consisting of a perchlorate salt, a p-toluenesulfonate salt, a tetrafluoroborate salt, and mixtures thereof.

15. The method of claim 11, wherein the reacting surface of an anode electrode used in the Kolbe electrolysis reaction is a platinum group metal, which includes platinum, iridium, palladium, ruthenium, rhodium, and osmium; or a carbon material, which includes graphite, glassy carbon, baked carbon; or mixture of the platinum group metal and the carbon material.

16. The method of claim 11, further comprising:
performing an olefin metathesis reaction on a hydrocarbon product of the Kolbe electrolysis reaction using a C2-C5 aliphatic alkene or a mixture of C2-C5 aliphatic alkenes, wherein the olefin metathesis reaction modifies a chain length of the hydrocarbon product.

17. The method of claim 11, further comprising:
performing an ethenolysis reaction on a hydrocarbon product of the Kolbe electrolysis reaction using ethene to obtain 1-decene, 1-heptene, 1-butene, 1-octene, 1-hexene, or 1,4-pentadiene.

18. The method of claim 17, further comprising:
separating the products of the ethenolysis reaction to obtain 1-decene, 1-heptene, 1-butene, 1-octene, 1-hexene, 1,4-pentadiene, a diesel fuel, and/or a heavy fuel oil.

19. The method of claim 11, further comprising:
hydroisomerizing at least some of the products from the Kolbe electrolysis reaction to produce a lubricant base oil, diesel fuels, jet fuel or gasoline-type products.

20. The method of claim 19, wherein the hydroisomerization reaction uses a catalyst which is a silica/alumina-based zeolite containing impregnated platinum, a reaction temperature between about 250° C. to about 400° C., a reaction pressure between about 10 bar to about 400 bar, and a hydrogen gas to a hydrocarbon ratio between about 2 to about 50.

* * * * *